US012694531B2

(12) United States Patent
Kaji et al.

(10) Patent No.: US 12,694,531 B2
(45) Date of Patent: Jul. 28, 2026

(54) DATA PROCESSING APPARATUS, DATA PROCESSING METHOD, AND DATA PROCESSING SYSTEM

(71) Applicant: J. MORITA MFG. CORP., Kyoto (JP)

(72) Inventors: Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 290 days.

(21) Appl. No.: 18/483,552

(22) Filed: Oct. 10, 2023

(65) Prior Publication Data

US 2024/0161300 A1 May 16, 2024

(30) Foreign Application Priority Data

Nov. 15, 2022 (JP) ................................. 2022-182608

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0066* (2013.01); *A61B 5/0071* (2013.01); *A61B 5/0088* (2013.01); *G06T 7/12* (2017.01); *G06T 7/55* (2017.01); *G06T 7/90* (2017.01); *G06T 12/10* (2026.01); *G06T 15/00* (2013.01);
(Continued)

(58) Field of Classification Search
CPC ........... G06T 7/0016; G06T 7/12; G06T 7/55; G06T 7/90; G06T 11/005; G06T 15/00;

G06T 2200/04; G06T 2207/10024; G06T 2207/10101; G06T 2207/30036; G06T 2210/41; G06T 2211/456; A61B 5/0066;
(Continued)

(56) References Cited

U.S. PATENT DOCUMENTS

2004/0197727 A1 10/2004 Sachdeva et al.
2007/0099147 A1 5/2007 Sachdeva et al.
(Continued)

FOREIGN PATENT DOCUMENTS

JP 2018-520804 A 8/2018
JP 2019-30587 A 2/2019
(Continued)

OTHER PUBLICATIONS

Extended European Search Report issued Apr. 3, 2024 in European Patent Application No. 23204047, 8 pages.
(Continued)

*Primary Examiner* — Bobbak Safaipour
*Assistant Examiner* — Dylan J Sherrillo
(74) *Attorney, Agent, or Firm* — Oblon, McClelland, Maier & Neustadt, L.L.P.

(57) ABSTRACT

A data processing apparatus includes input interface circuitry to which first three-dimensional data and second three-dimensional data indicating objects acquired at timings different from each other for a same person are input, and processing circuitry configured to compare pieces of soft tissue of at least one tooth between the first three-dimensional data and the second three-dimensional data using a shape of a crown portion of the at least one tooth included in the objects as a reference and output comparison information regarding a comparison result.

18 Claims, 13 Drawing Sheets

DATA PROCESSING APPARATUS
10

3

DATA PROCESSING SYSTEM
1

2

4

5

(51) Int. Cl.

| | |
|---|---|
| *G06T 7/12* | (2017.01) |
| *G06T 7/55* | (2017.01) |
| *G06T 7/90* | (2017.01) |
| *G06T 12/10* | (2026.01) |
| *G06T 15/00* | (2011.01) |

(52) U.S. Cl.
CPC .................... *G06T 2200/04* (2013.01); *G06T 2207/10024* (2013.01); *G06T 2207/10101* (2013.01); *G06T 2207/30036* (2013.01); *G06T 2210/41* (2013.01); *G06T 2211/456* (2023.08)

(58) Field of Classification Search
CPC ... A61B 5/0071; A61B 5/0088; A61C 9/0046; A61C 19/04; A61C 9/0053
See application file for complete search history.

(56) References Cited

U.S. PATENT DOCUMENTS

| | | | | |
|---|---|---|---|---|
| 2018/0078347 | A1* | 3/2018 | Falkel ...................... | A61B 1/24 |
| 2018/0168781 | A1 | 6/2018 | Kopelman et al. | |
| 2019/0231490 | A1 | 8/2019 | Sabina et al. | |
| 2019/0231491 | A1 | 8/2019 | Sabina et al. | |
| 2019/0231492 | A1 | 8/2019 | Sabina et al. | |
| 2019/0358002 | A1 | 11/2019 | Falkel | |
| 2020/0170762 | A1 | 6/2020 | Falkel | |
| 2020/0281697 | A1* | 9/2020 | Brandt ................... | G16H 30/20 |
| 2021/0186668 | A1 | 6/2021 | Falkel | |
| 2021/0205054 | A1 | 7/2021 | Sabina et al. | |
| 2021/0321872 | A1* | 10/2021 | Saphier ................. | A61B 5/004 |
| 2021/0353152 | A1 | 11/2021 | Saphier et al. | |
| 2021/0353153 | A1 | 11/2021 | Saphier et al. | |
| 2021/0353154 | A1 | 11/2021 | Saphier et al. | |
| 2022/0202295 | A1* | 6/2022 | Elbaz .................... | G16H 30/40 |
| 2023/0240820 | A1 | 8/2023 | Sabina et al. | |
| 2023/0320565 | A1 | 10/2023 | Falkel | |
| 2023/0372069 | A1 | 11/2023 | Sabina et al. | |

FOREIGN PATENT DOCUMENTS

| | | |
|---|---|---|
| JP | 2021-511160 A | 5/2021 |
| WO | WO-2017/013478 A1 | 1/2017 |
| WO | WO-2019/147884 A1 | 8/2019 |

OTHER PUBLICATIONS

Japanese Office Action issued Nov. 12, 2024 in Japanese Application No. 2022-182608, (with unedited computer-generated English translation), 8 pages.

Japanese Office Action issued Jan. 28, 2025 in Japanese Patent Application No. 2022-182608 (with unedited computer-generated English translation), 10 pages.

\* cited by examiner

DATA PROCESSING APPARATUS

10

DATA PROCESSING SYSTEM 1

Figure 4:
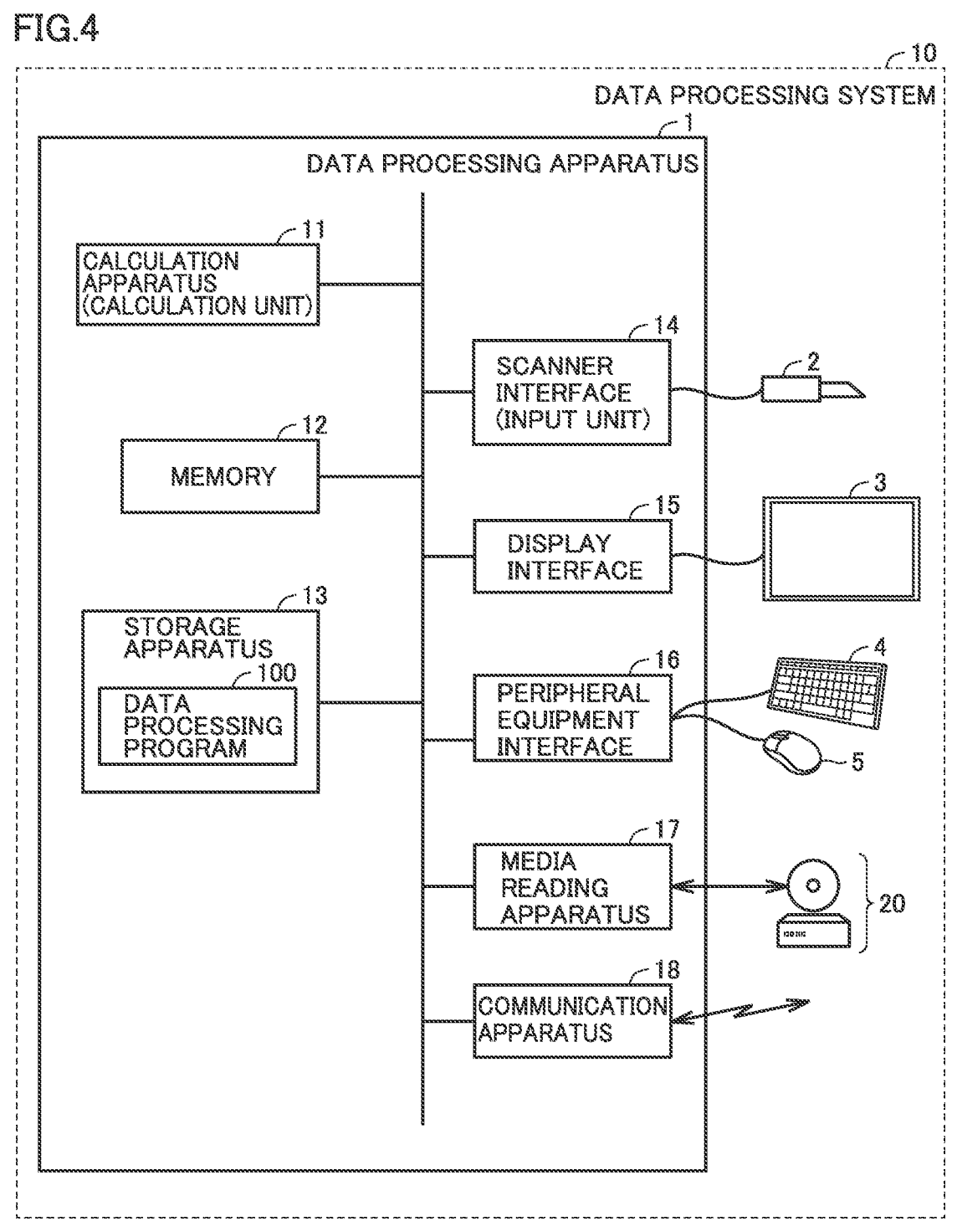

DATA PROCESSING SYSTEM — 10

DATA PROCESSING APPARATUS — 1

CALCULATION APPARATUS (CALCULATION UNIT) — 11

MEMORY — 12

STORAGE APPARATUS — 13

DATA PROCESSING PROGRAM — 100

SCANNER INTERFACE (INPUT UNIT) — 14

DISPLAY INTERFACE — 15

PERIPHERAL EQUIPMENT INTERFACE — 16

MEDIA READING APPARATUS — 17

COMMUNICATION APPARATUS — 18

2

3

4

5

20

TOOTH ROW
DIRECTION

ORTHOGONAL
DIRECTION

P

Q

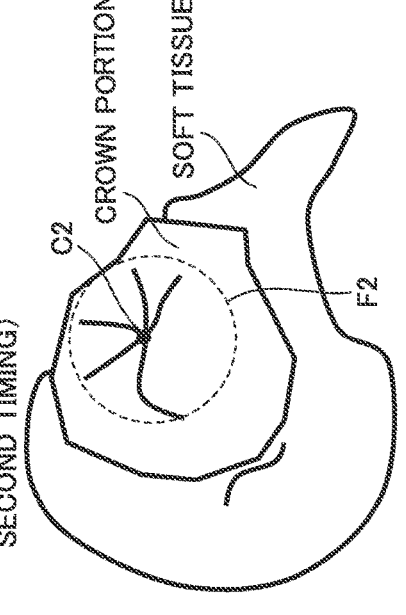
FIG. 6C
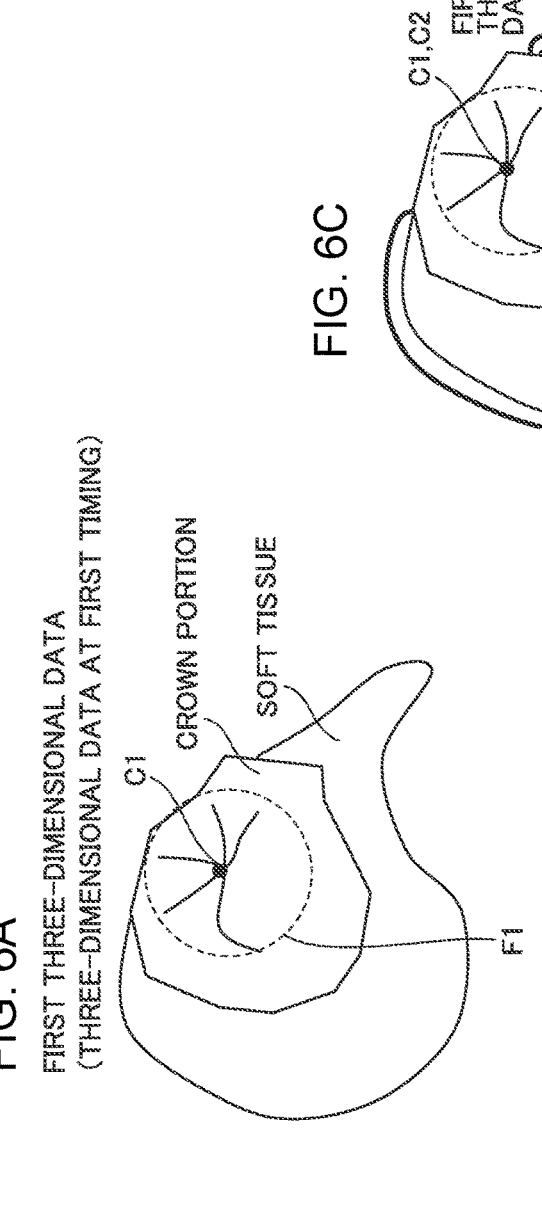
FIG. 6A
FIRST THREE-DIMENSIONAL DATA
(THREE-DIMENSIONAL DATA AT FIRST TIMING)
FIG. 6B
SECOND THREE-DIMENSIONAL DATA
(THREE-DIMENSIONAL DATA AT SECOND TIMING)

FIG.8

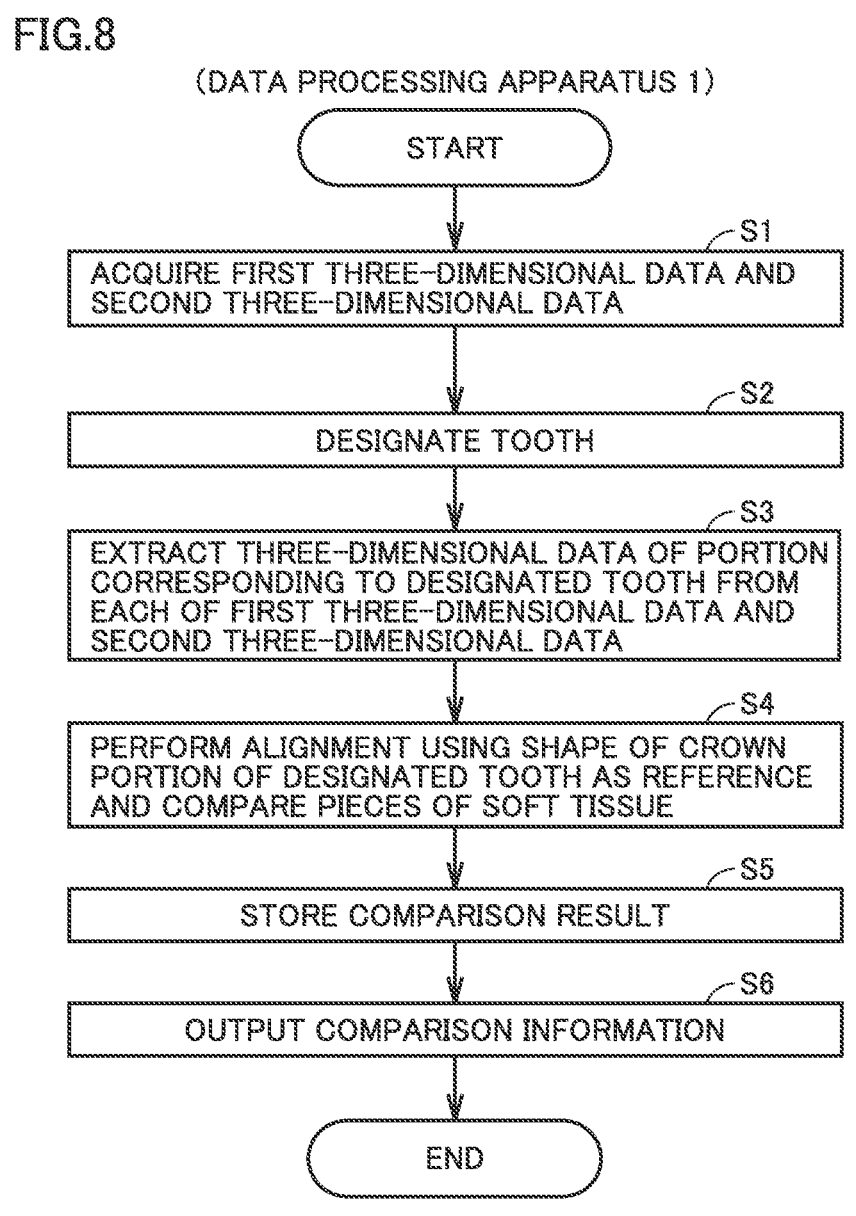

(DATA PROCESSING APPARATUS 1)

```
                    ┌──────────────┐
                    │    START     │
                    └──────────────┘
                            │
                            ▼               ╭─S1
    ┌───────────────────────────────────────────┐
    │ ACQUIRE FIRST THREE-DIMENSIONAL DATA AND   │
    │ SECOND THREE-DIMENSIONAL DATA              │
    └───────────────────────────────────────────┘
                            │
                            ▼               ╭─S2
    ┌───────────────────────────────────────────┐
    │            DESIGNATE TOOTH                 │
    └───────────────────────────────────────────┘
                            │
                            ▼               ╭─S3
    ┌───────────────────────────────────────────┐
    │ EXTRACT THREE-DIMENSIONAL DATA OF PORTION  │
    │ CORRESPONDING TO DESIGNATED TOOTH FROM     │
    │ EACH OF FIRST THREE-DIMENSIONAL DATA AND   │
    │ SECOND THREE-DIMENSIONAL DATA              │
    └───────────────────────────────────────────┘
                            │
                            ▼               ╭─S4
    ┌───────────────────────────────────────────┐
    │ PERFORM ALIGNMENT USING SHAPE OF CROWN     │
    │ PORTION OF DESIGNATED TOOTH AS REFERENCE   │
    │ AND COMPARE PIECES OF SOFT TISSUE          │
    └───────────────────────────────────────────┘
                            │
                            ▼               ╭─S5
    ┌───────────────────────────────────────────┐
    │          STORE COMPARISON RESULT           │
    └───────────────────────────────────────────┘
                            │
                            ▼               ╭─S6
    ┌───────────────────────────────────────────┐
    │       OUTPUT COMPARISON INFORMATION        │
    └───────────────────────────────────────────┘
                            │
                            ▼
                    ┌──────────────┐
                    │     END      │
                    └──────────────┘
```

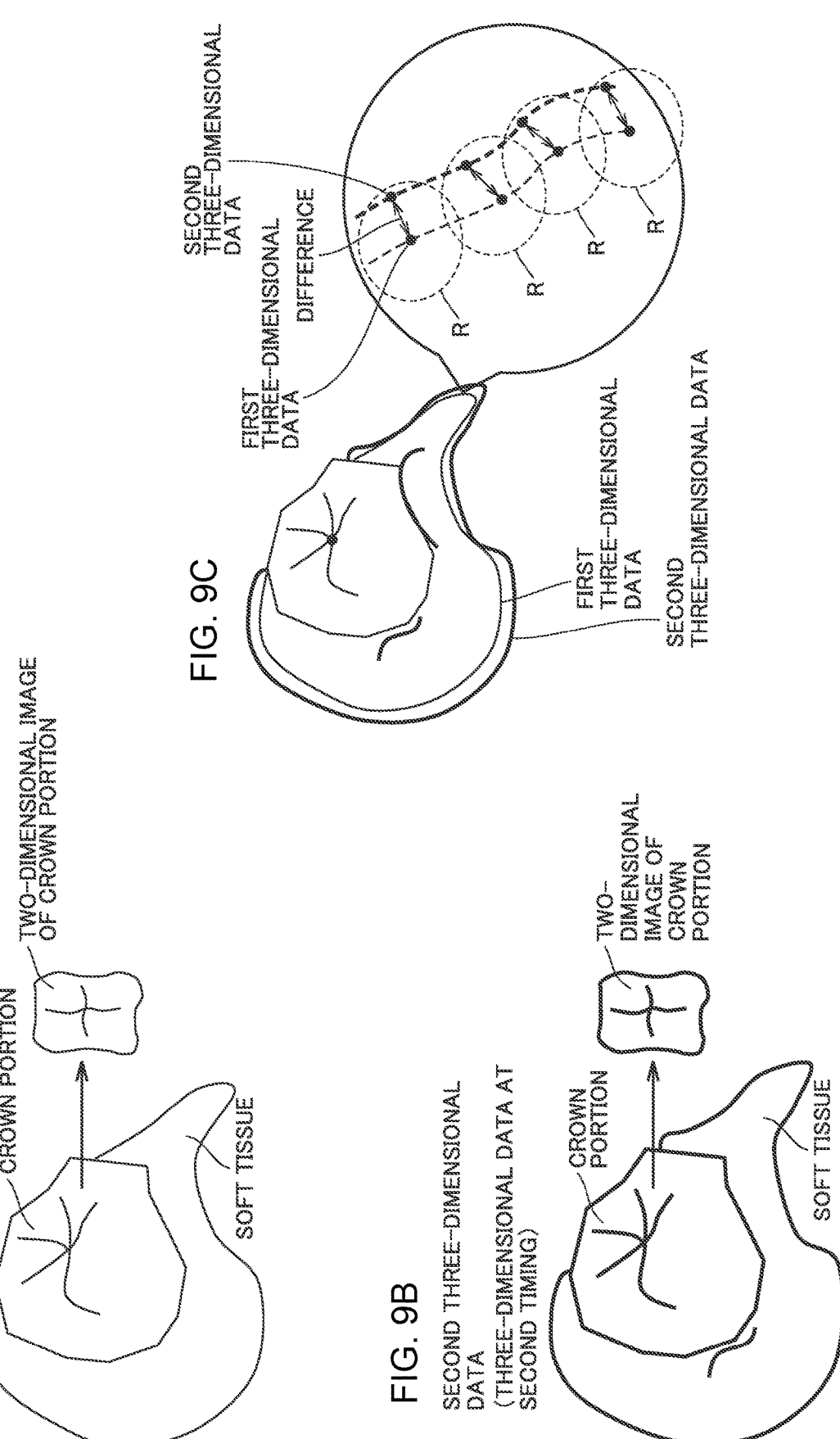

FIG. 9A
FIRST THREE-DIMENSIONAL DATA
(THREE-DIMENSIONAL DATA AT FIRST TIMING)

CROWN PORTION

TWO-DIMENSIONAL IMAGE OF CROWN PORTION

SOFT TISSUE

FIG. 9B
SECOND THREE-DIMENSIONAL DATA
(THREE-DIMENSIONAL DATA AT SECOND TIMING)

CROWN PORTION

TWO-DIMENSIONAL IMAGE OF CROWN PORTION

SOFT TISSUE

FIG. 9C

FIRST THREE-DIMENSIONAL DATA

SECOND THREE-DIMENSIONAL DATA

FIRST THREE-DIMENSIONAL DATA

SECOND THREE-DIMENSIONAL DATA

DIFFERENCE

R

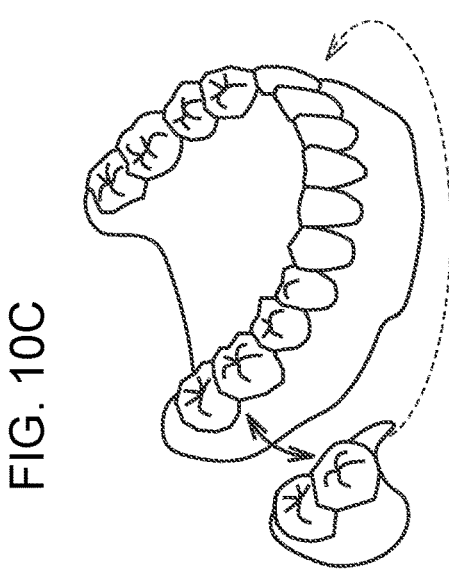
FIG. 10C
FIG. 10B
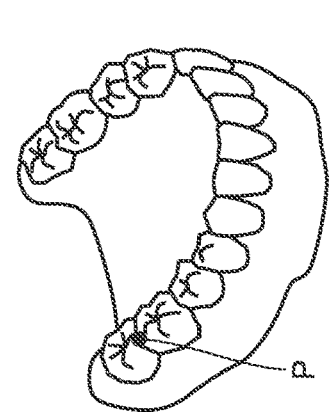
FIG. 10A

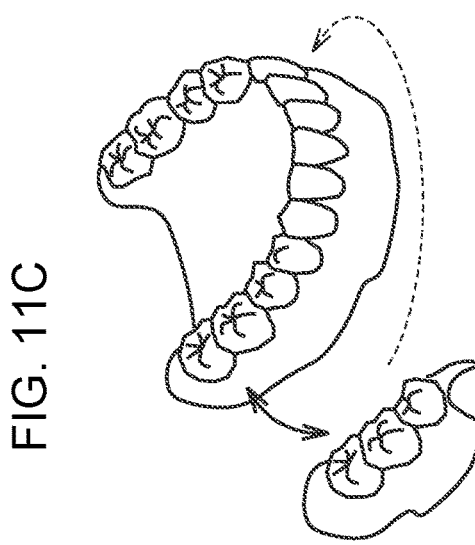
FIG. 11C
FIG. 11B
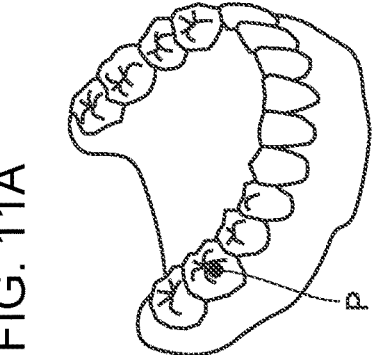
FIG. 11A

DESIGNATED TOOTH
(FIRST AND SECOND
THREE-DIMENSIONAL
DATA)

DESIGNATED TOOTH
(FIRST
THREE-DIMENSIONAL
DATA)

DESIGNATED TOOTH
(SECOND
THREE-DIMENSIONAL
DATA)

FIG.13

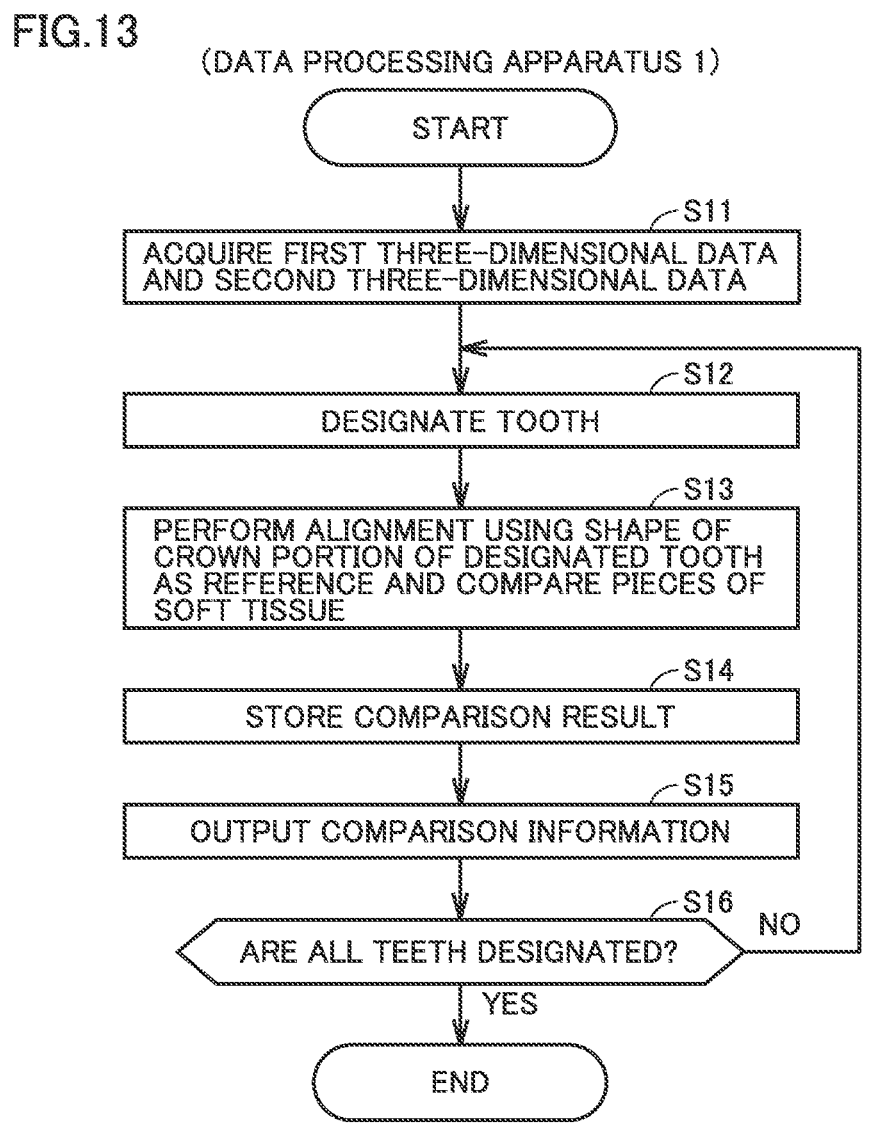

(DATA PROCESSING APPARATUS 1)

START

S11
ACQUIRE FIRST THREE-DIMENSIONAL DATA
AND SECOND THREE-DIMENSIONAL DATA

S12
DESIGNATE TOOTH

S13
PERFORM ALIGNMENT USING SHAPE OF
CROWN PORTION OF DESIGNATED TOOTH
AS REFERENCE AND COMPARE PIECES OF
SOFT TISSUE

S14
STORE COMPARISON RESULT

S15
OUTPUT COMPARISON INFORMATION

S16
ARE ALL TEETH DESIGNATED?    NO

YES

END

DATA PROCESSING APPARATUS, DATA PROCESSING METHOD, AND DATA PROCESSING SYSTEM

CROSS REFERENCE TO RELATED APPLICATIONS

This nonprovisional application is based on Japanese Patent Application No. 2022-182608 filed on Nov. 15, 2022, with the Japan Patent Office, the entire contents of which are hereby incorporated by reference.

BACKGROUND

Field of the Disclosure

The present disclosure relates to a data processing apparatus, a data processing method, and a data processing system that process three-dimensional data of an object inside an oral cavity.

Description of the Related Art

It is known that keeping teeth in a healthy condition is useful for extending healthy life expectancy. Thus, it is being studied to introduce mandatory annual dental checkups for all people, which is a so-called universal dental checkup. A practitioner such as a dentist also examines a health condition of the gums as well as a health condition of teeth in a dental checkup. The practitioner can find and treat diseases such as gingivitis, cavities or gum disease and can also prevent onset of these diseases by examining the condition of the gums.

Japanese Patent Laying-Open No. 2019-30587 discloses a gingivitis checkup system capable of determining a condition of gingivitis of a subject using a captured image obtained by capturing an image of inside of an oral cavity of the subject who is a diagnosis target.

SUMMARY

According to the system disclosed in Japanese Patent Laying-Open No. 2019-30587, the condition of gingivitis can be determined by comparing a color of the gums indicated in the captured image of the inside of the oral cavity and a color chart of the gums created from colors of the gums of a plurality of people. However, there are individual differences in the color of soft tissues such as the gums, and thus, whether or not the soft tissue of the subject is in a healthy condition cannot be accurately known through comparison between the color of the soft tissue and the color chart determined in advance, and whether or not the soft tissue of the subject is in a healthy condition cannot be accurately known unless a color of the soft tissue in the past and a current color of the soft tissue of the same subject are compared. Further, if a dental checkup is conducted every year by introduction of the universal dental checkup, it is important to know the annual change in a condition of the soft tissue inside the oral cavity.

The present disclosure has been made to solve such a problem and is directed to providing a technique capable of temporally comparing the soft tissue inside the oral cavity.

According to one example of the present disclosure, a data processing apparatus that processes three-dimensional data of objects inside an oral cavity is provided. The data processing apparatus includes an input unit to which first three-dimensional data and second three-dimensional data indicating the objects acquired at timings different from each other for a same person are input, and a calculation unit that compares soft tissue of at least one tooth between the first three-dimensional data and the second three-dimensional data using a shape of a crown portion of the at least one tooth included in the objects as a reference and outputs comparison information regarding a comparison result.

According to one example of the present disclosure, a data processing method for processing three-dimensional data of objects inside an oral cavity by a computer is provided. The data processing method includes, as processing to be executed by the computer, acquiring first three-dimensional data and second three-dimensional data indicating the objects acquired at timings different from each other for a same person, comparing soft tissue of at least one tooth between the first three-dimensional data and the second three-dimensional data using a shape of a crown portion of the at least one tooth included in the objects as a reference, and outputting comparison information regarding a comparison result.

According to one example of the present disclosure, a data processing program of processing three-dimensional data of objects inside an oral cavity is provided. The data processing program causes a computer to execute acquiring first three-dimensional data and second three-dimensional data indicating the objects acquired at timings different from each other for a same person, comparing soft tissue of at least one tooth between the first three-dimensional data and the second three-dimensional data using a shape of a crown portion of the at least one tooth included in the objects as a reference, and outputting comparison information regarding a comparison result.

According to one example of the present disclosure, a data processing system that processes three-dimensional data of objects inside an oral cavity is provided. The data processing system includes a three-dimensional scanner that acquires the three-dimensional data of the objects, and a data processing apparatus that processes the three-dimensional data acquired by the three-dimensional scanner. The data processing apparatus includes an input unit to which first three-dimensional data and second three-dimensional data indicating objects acquired at timings different from each other for a same person are input, and a calculation unit that compares soft tissue of at least one tooth between the first three-dimensional data and the second three-dimensional data using a shape of a crown portion of the at least one tooth included in the objects as a reference and outputs comparison information regarding a comparison result.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 4 is a block diagram illustrating a hardware configuration of the data processing system and the data processing apparatus according to the first embodiment.

FIG. 6A is a view for explaining an example of comparison of soft tissue to be executed by the data processing apparatus according to the first embodiment.

FIG. 6B is a view for explaining an example of comparison of soft tissue to be executed by the data processing apparatus according to the first embodiment.

FIG. 6C is a view for explaining an example of comparison of soft tissue to be executed by the data processing apparatus according to the first embodiment.

FIG. 8 is a flowchart of the comparison processing of the soft tissue to be executed by the data processing apparatus according to the first embodiment.

FIG. 9A is a view for explaining an example of comparison of soft tissue to be executed by a data processing apparatus according to a second embodiment.

FIG. 9B is a view for explaining an example of comparison of soft tissue to be executed by a data processing apparatus according to a second embodiment.

FIG. 9C is a view for explaining an example of comparison of soft tissue to be executed by a data processing apparatus according to a second embodiment.

FIG. 10A is a view for explaining extraction of three-dimensional data to be subjected to comparison processing according to a third embodiment.

FIG. 10B is a view for explaining extraction of three-dimensional data to be subjected to comparison processing according to a third embodiment.

FIG. 10C is a view for explaining extraction of three-dimensional data to be subjected to comparison processing according to a third embodiment.

FIG. 11A is a view for explaining extraction of three-dimensional data to be subjected to comparison processing according to a fourth embodiment.

FIG. 11B is a view for explaining extraction of three-dimensional data to be subjected to comparison processing according to a fourth embodiment.

FIG. 11C is a view for explaining extraction of three-dimensional data to be subjected to comparison processing according to a fourth embodiment.

FIG. 13 is a flowchart of the comparison processing of soft tissue to be executed by a data processing apparatus according to the fifth embodiment.

DETAILED DESCRIPTION

First Embodiment

Figure 1:
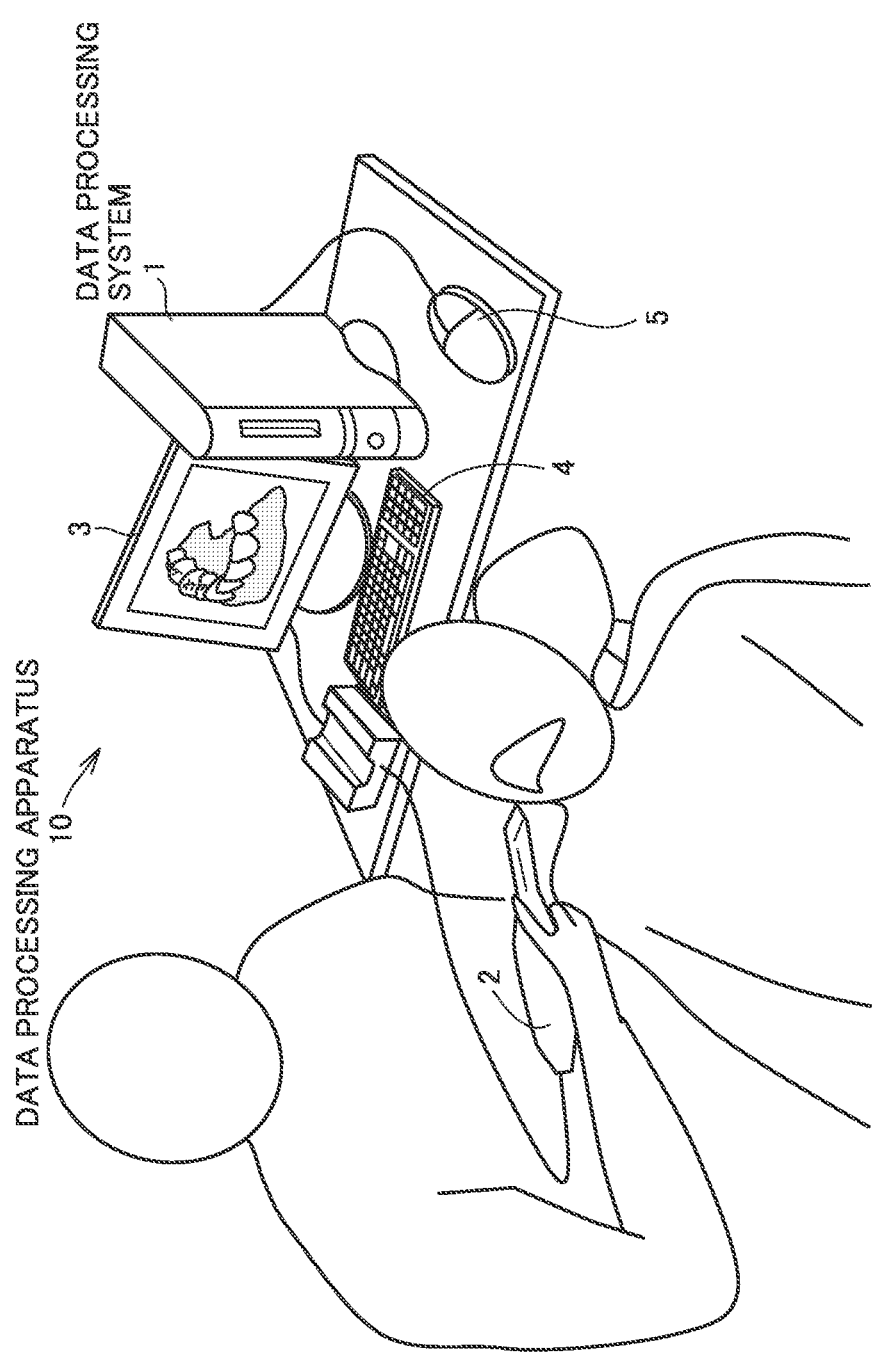
FIG. 1 is a view illustrating an application example of a data processing system and a data processing apparatus according to a first embodiment.

Embodiments of the present disclosure will be described in detail with reference to the drawings. Note that the same or corresponding portions in the drawings will be denoted by the same reference numerals, and redundant description will be omitted.

Application Example

An application example of a data processing system 10 and a data processing apparatus 1 according to a first embodiment will be described with reference to FIG. 1 to FIG. 3E. FIG. 1 is a view illustrating the application example of data processing system 10 and data processing apparatus 1 according to the first embodiment.

As illustrated in FIG. 1, data processing system 10 according to the first embodiment includes data processing apparatus 1 and a three-dimensional scanner 2. A user can acquire three-dimensional data indicating shapes of a plurality of objects inside an oral cavity by scanning inside the oral cavity of a subject using three-dimensional scanner 2. Data processing apparatus 1 is connected so as to be able to perform communication with three-dimensional scanner 2 and processes the three-dimensional data acquired by three-dimensional scanner 2.

The "user" may be anyone such as a practitioner such as a dentist, a dental assistant, a professor or a student of a dental university, a dental technician, an engineer of a manufacturer and a worker at a manufacturing factory, who acquires three-dimensional data of objects such as teeth and soft tissue using three-dimensional scanner 2. The "subject" may be anyone such as a patient at a dental clinic, and a subject in a dental university, who can be a target to be scanned by three-dimensional scanner 2.

The "object" to be scanned may be anything such as a row of teeth of the upper jaw or the lower jaw inside the oral cavity, that can be a target to be scanned by three-dimensional scanner 2. The "row of teeth" includes teeth and soft tissue located around the teeth. The "teeth" includes natural teeth and artificial teeth (such as prosthesis and implant). The "soft tissue" includes at least the gums. Note that the "soft tissue" may include the buccal mucous membrane. The buccal mucous membrane may include a lump on the mucous membrane occurring by mouth inflammation or a malignant tumor.

Three-dimensional scanner 2 is a so-called intra oral scanner (IDS) capable of optically capturing an image of inside of the oral cavity of the subject using a confocal method or a triangulation method. Specifically, three-dimensional scanner 2 acquires position information (coordinates of respective axes of a longitudinal direction, a lateral direction and a height direction) of each point of a point cloud (a plurality of points) representing surface shapes of targets to be scanned (objects) as the three-dimensional data using an optical sensor, or the like, by scanning the objects inside the oral cavity. In other words, the three-dimensional data is position data (IOS data) including the position information of each point of the point cloud that constitutes surfaces of the objects placed on a certain coordinate space. Further, three-dimensional scanner 2 acquires color information indicating a color of each of the point cloud (a plurality of points) representing the shape of the targets to be scanned (objects) as the three-dimensional data by scanning the objects inside the oral cavity. In other words, the three-dimensional data includes color information of each point of the point cloud in association with the position information of each point of the point cloud that constitutes the surfaces of the objects. Note that hereinafter, the position information of each point of the point cloud that constitutes the surfaces of the targets to be scanned (objects) will be also simply referred to as "three-dimensional data".

Data processing apparatus 1 generates a two-dimensional image indicating two-dimensional objects viewed from an arbitrary point of view on the basis of the three-dimensional data of the objects acquired by three-dimensional scanner 2. Such a two-dimensional image, which is generated by processing or editing the three-dimensional data, is also referred to as a "rendering image". Data processing apparatus 1 can show the surfaces of the objects inside the oral cavity viewed from an arbitrary point of view to the user by displaying the generated rendering image on a display 3.

According to data processing system 10 as described above, for example, the user can display a two-dimensional rendering image indicating rows of teeth of the upper jaw and the lower jaw viewed from an arbitrary point of view on display 3 by scanning the rows of teeth of the upper jaw and the lower jaw inside the oral cavity using three-dimensional scanner 2.

Figure 2:
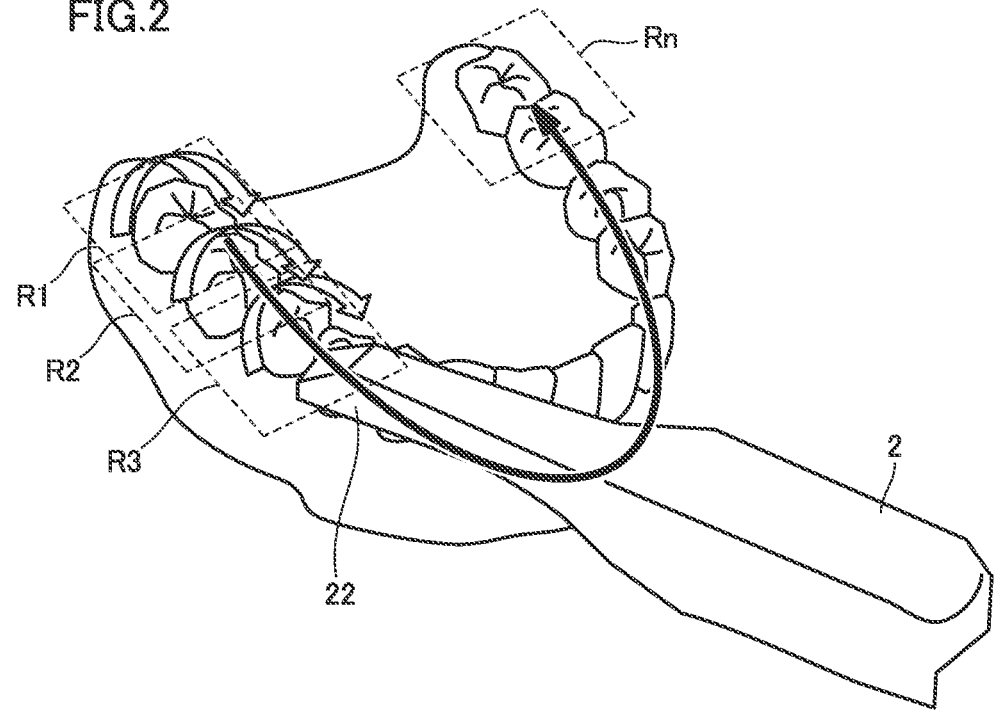
FIG. 2 is a view for explaining a method for scanning inside an oral cavity using a three-dimensional scanner.

A method for scanning inside the oral cavity using three-dimensional scanner 2 will be described with reference to FIG. 2. FIG. 2 is a view for explaining the method for scanning inside the oral cavity using three-dimensional scanner 2. A scanning range of three-dimensional scanner 2 is limited by a size of a probe 22 that can be inserted into the oral cavity. Thus, the user inserts probe 22 of three-dimensional scanner 2 inside the oral cavity, performs scanning while moving probe 22 along the row of teeth inside the oral cavity to scan inside the oral cavity separately a plurality of times.

For example, as illustrated in FIG. 2, the user acquires three-dimensional data of the objects inside the oral cavity by sequentially switching the scanning range to R1, R2, R3, . . . , Rn by moving probe 22 inside the oral cavity. More specifically, the user scans part of the teeth and soft tissue (such as, for example, the gums around the part of the teeth) corresponding to the teeth by moving probe 22 from a labial surface of the teeth to a lingual surface of the teeth by way of an occlusal surface and sequentially performs such scanning for a plurality of teeth and soft tissue corresponding to the teeth by moving probe 22 from one back tooth side to the other back tooth side by way of the front teeth. Note that a way of moving probe 22 inside the oral cavity is different for each user or each dental practice, and thus, objects inside the oral cavity for which three-dimensional data is to be acquired and order of acquisition can vary.

Generation of the three-dimensional data will be described with reference to FIG. 3A to FIG. 3E. FIGS. 3A-3E show views for explaining generation of the three-dimensional data indicating shapes of teeth and soft tissue inside the oral cavity. As illustrated in FIG. 3A, FIG. 3B, FIG. 3C and FIG. 3D, data processing apparatus 1 generates three-dimensional data of the whole row of teeth including a plurality of teeth and the gums by connecting the three-dimensional data acquired by three-dimensional scanner 2.

The three-dimensional data generated as described above can indicate a shape of the soft tissue corresponding to the whole row of teeth. Thus, data processing apparatus 1 can detect change in a condition of the soft tissue by comparing first three-dimensional data and second three-dimensional data indicating objects inside the oral cavity, acquired at timings different from each other for a same person. For example, data processing apparatus 1 can detect change in a condition of the soft tissue in one year by comparing the first three-dimensional data indicating the objects inside the oral cavity of the subject acquired one year ago and the second three-dimensional data indicating the objects inside the oral cavity of the same subject acquired this year. The "condition of the soft tissue" includes at least one of a shape of the soft tissue and a color of the soft tissue.

Here, as illustrated in FIG. 2, while the user connects the three-dimensional data of respective portions inside the oral cavity as illustrated in FIG. 3A to FIG. 3D after scanning the objects inside the oral cavity separately in a plurality of stages from an end on one side of the row of teeth to an end of the other side, there is a case where a shape of the whole row of teeth indicated with the three-dimensional data generated by the connection may be different from an actual shape of the whole row of teeth. This is because when the three-dimensional data of the respective portions inside the oral cavity are connected, an error occurs between the connected data and the real objects (e.g., teeth). Further, as the number of times of connection increases, such an error becomes larger.

More specifically, in the three-dimensional data connected as illustrated in FIG. 3A to FIG. 3D, while a difference between a shape of a first tooth indicated in the three-dimensional data connected earlier and an actual shape of the first tooth is small, a difference between a shape of a second tooth indicated in the three-dimensional data connected later and an actual shape of the second tooth is likely to be larger.

Figure 3D:
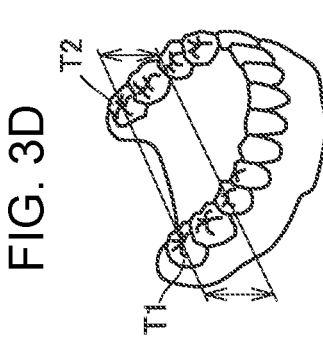
FIG. 3D is a view for explaining generation of three-dimensional data indicating shapes of teeth and soft tissue inside the oral cavity.
Figure 3E:
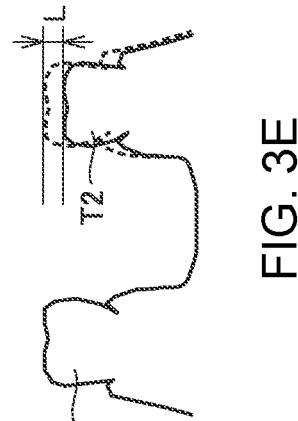
FIG. 3E is a view for explaining generation of three-dimensional data indicating shapes of teeth and soft tissue inside the oral cavity.
Figure 3C:
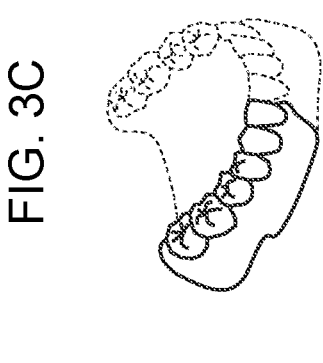
FIG. 3C is a view for explaining generation of three-dimensional data indicating shapes of teeth and soft tissue inside the oral cavity.
Figure 3B:
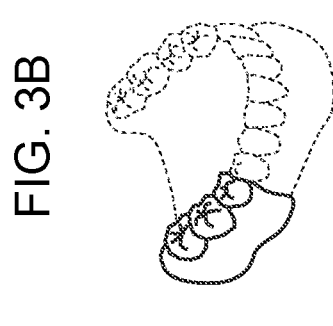
FIG. 3B is a view for explaining generation of three-dimensional data indicating shapes of teeth and soft tissue inside the oral cavity.
Figure 3A:
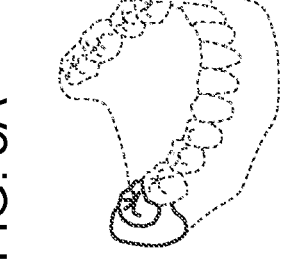
FIG. 3A is a view for explaining generation of three-dimensional data indicating shapes of teeth and soft tissue inside the oral cavity.

For example, as illustrated in FIG. 3D and FIG. 3E, while a height of a first tooth T1 indicated in the three-dimensional data connected earlier tends to substantially match an actual height of first tooth T1, a height of a tooth T2 indicated in the three-dimensional data connected later tends to be largely different from an actual height of second tooth T2. In the example in FIG. 3E, there is a possibility that the height of tooth T2 (a tooth indicated with a solid line) indicated in the three-dimensional data becomes lower (or higher) than the actual height of second tooth T2 (a tooth indicated with a dashed line) by an amount corresponding to an error L of several millimeters. In a case where scanning is performed along a tooth row direction, such error L can become greater for a tooth located at a position farther from a tooth scanned first in the tooth row direction. Further, such error L occurs when the three-dimensional data of the respective portions inside the oral cavity are connected, and thus, error L does not always become the same value every time. In other words, error L as described above does not always become the same between the first three-dimensional data indicating the objects inside the oral cavity of the subject, acquired one year ago and the second three-dimensional data indicating the objects inside the oral cavity of the same subject, acquired this year.

Thus, to detect change in a condition of soft tissue such as the gums in one year, when the first three-dimensional data indicating the objects inside the oral cavity of the subject, acquired one year ago, and the second three-dimensional data indicating the objects inside the oral cavity of the same subject, acquired this year, are compared, in a case where the whole row of teeth in the both data is simply compared, there is a possibility that change in the condition of the soft tissue cannot be detected with high accuracy due to error L being not constant.

Thus, data processing apparatus 1 according to the first embodiment is configured to compare the soft tissue around at least one tooth (a predetermined range of soft tissue that contacts the at least one tooth) between the first three-dimensional data and the second three-dimensional data using a shape of a crown portion of the at least one tooth included in the objects as a reference instead of comparing the whole objects inside the oral cavity between the first three-dimensional data and the second three-dimensional data indicating the objects inside the oral cavity, acquired at timings different from each other for the same person. Comparison processing of the soft tissue to be executed by data processing apparatus 1 will be specifically described below.

Hardware Configuration of Data Processing Apparatus

A hardware configuration of data processing system 10 and data processing apparatus 1 according to the first embodiment will be described with reference to FIG. 4. FIG. 4 is a block diagram illustrating the hardware configuration of data processing system 10 and data processing apparatus 1 according to the embodiment. Data processing apparatus 1 may be, for example, implemented by a general-purpose computer or may be implemented by a computer dedicated for data processing system 10.

As illustrated in FIG. 4, data processing apparatus 1 includes a calculation apparatus 11, a memory 12, a storage apparatus 13, a scanner interface 14, a display interface 15, a peripheral equipment interface 16, a media reading apparatus 17 and a communication apparatus 18 as main hardware elements.

Calculation apparatus 11 has a function of a "calculation unit" and includes a computer such as a processor. The processor includes, for example, a microcontroller, a central processing unit (CPU), a micro-processing unit (MPU), or the like. Note that while the processor has functions of executing various kinds of processing by executing programs, part or all of these functions may be implemented using a dedicated hardware circuit such as an application specific integrated circuit (ASIC), a graphics processing unit (GPU) or a field-programmable gate array (FPGA). The "processor" is not limited to a narrowly defined processor that executes processing in a stored program scheme, like a CPU or an MPU and can include a hardwired circuit such as an ASIC or an FPGA. Thus, the processor can read as processing circuitry for which processing is defined in advance by a computer-readable code and/or a hardwired circuit. Note that the processor may be constituted with one chip or may be constituted with a plurality of chips. Further, the processor and the related processing circuitry may be constituted with a plurality of computers interconnected in a wired or wireless manner via a local area network or a wireless network. The processor and the related processing circuitry may be constituted with a cloud computer that remotely performs calculation on the basis of input data and outputs a calculation result to another device located at a separate position.

Memory 12 provides a storage area for storing a program code, a work memory, or the like, when the processor of calculation apparatus 11 executes various kinds of programs. Memory 12 may be one or a plurality of non-transitory computer readable medium. Examples of memory 12 can include a volatile memory such as a dynamic random access memory (DRAM) and a static random access memory (SRAM) or a non-volatile memory such as a read only memory (ROM) and a flash memory.

Storage apparatus 13 provides a storage area for storing various kinds of programs that can be read and executed by the processor of calculation apparatus 11 and various kinds of data. Storage apparatus 13 may be one or a plurality of computer readable storage medium. Examples of storage apparatus 13 can include a storage apparatus such as a hard disk drive (HDD) and a solid state drive (SSD).

Storage apparatus 13 stores a data processing program 100. Data processing program 100 is a program describing a content of comparison processing for comparing the soft tissue on the basis of the three-dimensional data of the objects inside the oral cavity acquired by three-dimensional scanner 2 and can be read and executed by calculation apparatus 11. Data processing program 100 may be input by the user using a keyboard 4 and a mouse 5 and executed, may be read from a recording medium 20 by media reading apparatus 17 or may be acquired from other apparatuses such as a server by communication apparatus 18 via a network.

Scanner interface 14 is an interface having a function of an "input unit" and connecting three-dimensional scanner 2. Scanner interface 14 may be constituted with an input circuitry. Scanner interface 14 implements input/output of data between data processing apparatus 1 and three-dimensional scanner 2. Data processing apparatus 1 is connected to three-dimensional scanner 2 in a wired manner using a cable or in a wireless manner (such as WiFi and BlueTooth (registered trademark)).

Display interface 15 is an interface for connecting display 3 and implements input/output data between data processing apparatus 1 and display 3.

Peripheral equipment interface 16 is an interface for connecting peripheral equipment such as keyboard 4 and mouse 5 and implements input/output of data between data processing apparatus 1 and the peripheral equipment.

Media reading apparatus 17 reads out data stored in recording medium 20 or writes data in recording medium 20. Recording medium 20 is a non-transitory and tangible computer readable storage medium and may take any form such as a compact disc (CD), a digital versatile disc (DVD) or a universal serial bus (USB) memory if the medium can record various kinds of data. In the embodiment, recording medium 20 can store data processing program 100, and calculation apparatus 11 can execute data processing program 100 read out from recording medium 20.

Communication apparatus 18 transmits/receives data to/from an external apparatus through wired communication or wireless communication. For example, communication apparatus 18 can transmit comparison information corresponding to a comparison result of the soft tissue to a server apparatus by being connected so as to be able to perform communication with a hospital server or a server outside a hospital (for example, a cloud server) in a wired manner using a cable or in a wireless manner (such as WiFi and BlueTooth (registered trademark)).

Extraction of Three-Dimensional Data to be Subjected to Comparison Processing Extraction of three-dimensional data to be subjected to comparison processing to be executed by data processing apparatus 1 will be described with reference to FIG. 5A and

US 12,694,531 B2

9

Figure 5B:
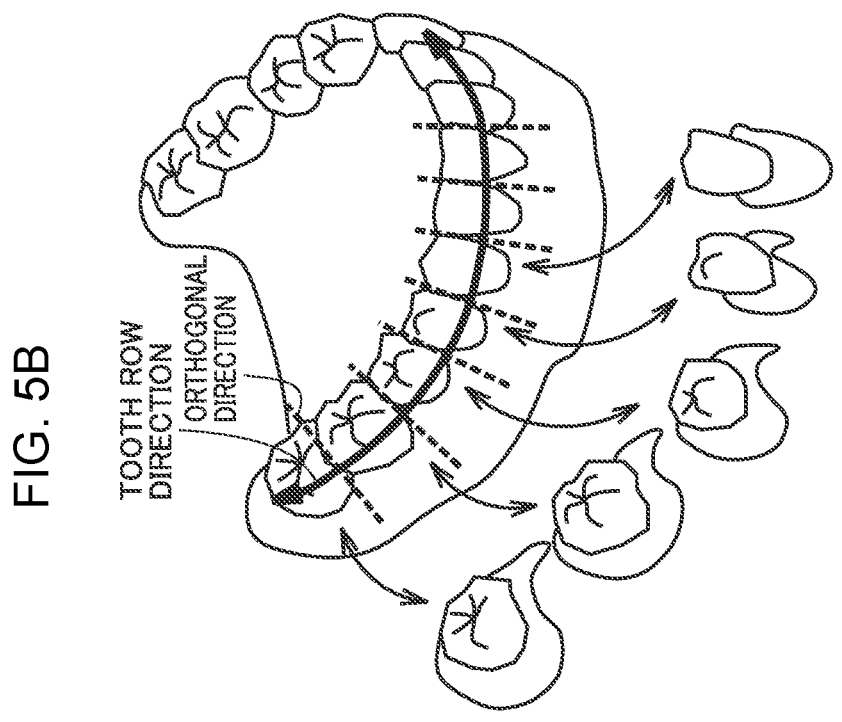
FIG. 5B is a view for explaining extraction of three-dimensional data to be subjected to comparison processing according to the first embodiment.

FIG. 5B. FIGS. 5A-5B illustrate a view for explaining extraction of three-dimensional data to be subjected to the comparison processing according to the first embodiment.

Figure 5A:
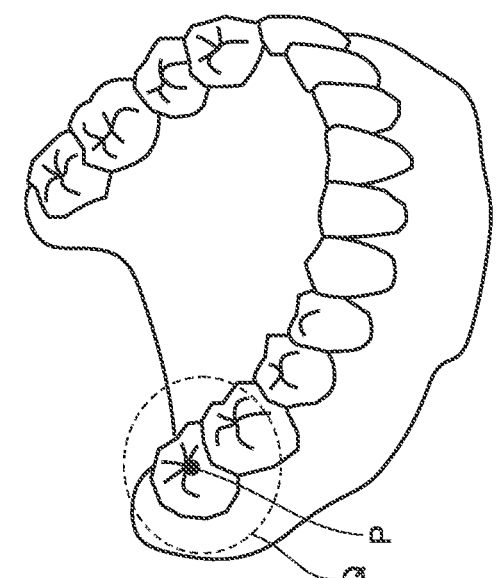
FIG. 5A is a view for explaining extraction of three-dimensional data to be subjected to comparison processing according to the first embodiment.

As illustrated in FIGS. 5A-5B, data processing apparatus 1 extracts three-dimensional data indicating at least one tooth and soft tissue corresponding to the at least one tooth (such as, for example, the gum around the at least one tooth) from the generated three-dimensional data indicating the whole row of teeth as a comparison target of the comparison processing. In other words, data processing apparatus 1 extracts three-dimensional data indicating at least one tooth and soft tissue corresponding to the at least one tooth by dividing the three-dimensional data indicating the whole row of teeth.

Specifically, as illustrated in FIG. 5A, data processing apparatus 1 designates a portion for which the three-dimensional data is to be extracted among the objects inside the oral cavity as a designated point P and extracts three-dimensional data at a portion enclosed as a predetermined range Q including designated point P. Then, as illustrated in FIG. 5B, data processing apparatus 1 extracts three-dimensional data of each portion while switching a portion for which three-dimensional data is to be extracted by moving a position of designated point P along the row of teeth.

For example, in the example in FIG. 5A, data processing apparatus 1 designates one tooth as designated point P among a plurality of teeth included in the generated whole row of teeth. More specifically, data processing apparatus 1 designates a center of one tooth (for example, a center of a crown portion) as designated point P. Data processing apparatus 1 extracts three-dimensional data of a portion enclosed as predetermined range Q including designated point P having been designated. Then, data processing apparatus 1 designates the adjacent next tooth as designated point P by moving the position of designated point P along the row of teeth and extracts three-dimensional data of a portion enclosed as range Q including designated point P. In this event, data processing apparatus 1 extracts three-dimensional data of the portion enclosed as range Q including designated point P so that the row of teeth is divided in a direction substantially orthogonal to a tooth row direction of an arch of the teeth. In this manner, data processing apparatus 1 extracts three-dimensional data of each portion while switching the portion for which the three-dimensional data is to be extracted as illustrated in FIG. 5B. The three-dimensional data extracted in this manner includes three-dimensional data indicating each tooth and soft tissue corresponding to each tooth (such as, for example, the gum around at least one tooth).

Note that data processing apparatus 1 may determine the portion for which the three-dimensional data is to be extracted in accordance with designation by the user. For example, the user may set a portion for which the user desires to detect change in the condition of the soft tissue as designated point P. Data processing apparatus 1 may extract three-dimensional data of a portion enclosed as range Q including designated point P on the basis of designated point P set by the user.

Data processing apparatus 1 may determine the portion for which the three-dimensional data is to be extracted in accordance with predetermined order set in advance by the user. For example, the user may set the teeth for which the user desires to extract the three-dimensional data as designated point P in predetermined order. Data processing apparatus 1 may set designated point P in the predetermined order set by the user and extract the three-dimensional data of a portion enclosed as range Q including designated point P in the predetermined order.

Data processing apparatus 1 may determine the portion for which the three-dimensional data is to be extracted in accordance with a data amount of the three-dimensional data to be extracted. For example, data processing apparatus 1 may extract three-dimensional data of a first portion (for example, a first tooth) and in a case where a data amount of the extracted three-dimensional data exceeds a predetermined amount, may extract three-dimensional data of the next second portion (for example, a second tooth adjacent to the first tooth). In this manner, data processing apparatus 1 may extract the three-dimensional data for each predetermined data amount.

Data processing apparatus 1 may determine the portion for which the three-dimensional data is to be extracted on the basis of colors of the objects. For example, data processing apparatus 1 may set designated point P for each of the objects of the same or substantially the same color and extract three-dimensional data of a portion enclosed as predetermined range Q including designated point P. Note that data processing apparatus 1 only needs to determine a color of the portion corresponding to each piece of three-dimensional data on the basis of color information of the objects to be scanned included in the three-dimensional data.

Data processing apparatus 1 may divide the three-dimensional data for each tooth by executing edge extraction processing on a boundary portion between a tooth and the gum and the adjacent tooth.

Data processing apparatus 1 may divide the generated whole row of teeth for each tooth using artificial intelligence (AI). Then, data processing apparatus 1 may set designated point P for each of the divided teeth and extract three-dimensional data of a portion enclosed as predetermined range Q including designated point P. The AI is constituted with an estimation model trained through machine learning so that each of a plurality of teeth included in a row of teeth is identified on the basis of three-dimensional data corresponding to the row of teeth. The estimation model includes, for example, a publicly known neural network to be used in recognition processing through deep learning such as a convolution neural network (CNN), a generative adversarial network (GAN), a recurrent neural network (RNN) and a long short-term memory network (LSTM network), and parameters regarding the neural network. Concerning training of the estimation model, please see Japanese Patent No. 6650996.

Data processing apparatus 1 may determine range Q in accordance with designation by the user. For example, the user may input range data for designating a range for which the user desires to detect change in the condition of the soft tissue to data processing apparatus 1. Data processing apparatus 1 may set range Q on the basis of the range data input by the user and extract three-dimensional data of a portion enclosed as range Q including designated point P. For example, range Q may be a range of 360° centered on designated point P.

Example of Comparison of Soft Tissue

Comparison of the soft tissue in the comparison processing to be executed by data processing apparatus 1 will be described with reference to FIGS. 6A-6C. FIGS. 6A-6C illustrate a view for explaining an example of comparison of the soft tissue to be executed by data processing apparatus 1 according to the first embodiment.

As illustrated in FIG. 6C, data processing apparatus 1 compares soft tissue around at least one tooth (a predetermined range of the soft tissue that contacts the tooth) between the first three-dimensional data and the second three-dimensional data using a shape of a crown portion of the at least one tooth included in the objects as a reference using the first three-dimensional data and the second three-dimensional data indicating the objects inside the oral cavity, acquired at timings different from each other for the same person.

Specifically, data processing apparatus 1 extracts three-dimensional data of one tooth and the soft tissue corresponding to the tooth from the three-dimensional data acquired at a first timing using the method illustrated in FIGS. 5A-5B. As illustrated in FIG. 6A, the extracted three-dimensional data at the first timing will be also referred to as the first three-dimensional data. Further, data processing apparatus 1 extracts three-dimensional data of the one tooth that is the same as the tooth at the first timing and the soft tissue corresponding to the tooth from three-dimensional data acquired at a second timing (for example, a timing one year later from the first timing) after the first timing using the method illustrated in FIGS. 5A-5B. As illustrated in FIG. 6B, the extracted three-dimensional data at the second timing will be also referred to as the second three-dimensional data. Data processing apparatus 1 can generate a rendering image indicating the one tooth and the soft tissue corresponding to the tooth on the basis of each of the first three-dimensional data and the second three-dimensional data. Note that data processing apparatus 1 can indicate a color of the soft tissue with the rendering image in addition to the shape of the soft tissue on the basis of the first three-dimensional data and the second three-dimensional data.

Data processing apparatus 1 sets a predetermined position as a center position C1 in the crown portion of the tooth indicated with the first three-dimensional data and specifies a shape of the crown portion enclosed as a predetermined range F1 from center position C1. Further, data processing apparatus 1 sets a predetermined position as a center position C2 in the crown portion of the tooth indicated with the second three-dimensional data and specifies a shape of the crown portion enclosed as a predetermined range F2 from center position C2. Center positions C1 and C2 are determined in advance and are, for example, center positions of the crown portion of the tooth. Further, ranges F1 and F2 are determined in advance and are, for example, regions of 60% of an occlusal surface indicated in a case where the crown portion is viewed in planar view. Note that ranges F1 and F2 may be the whole region of the occlusal surface indicated in a case where the crown portion is viewed in planar view.

As illustrated in FIG. 6C, data processing apparatus 1 superimposes the one tooth and the soft tissue indicated with the first three-dimensional data on the one tooth and the soft tissue indicated with the second three-dimensional data and compares the both. In this event, data processing apparatus 1 superimposes the one tooth and the soft tissue indicated with the first three-dimensional data on the one tooth and the soft tissue indicated with the second three-dimensional data while aligning the crown portion enclosed as range F1 specified in the first three-dimensional data with the crown portion enclosed as range F2 specified in the second three-dimensional data. The crown portion is hard tissue, and thus, a shape of the crown portion is less likely to temporally change unlike with soft tissue such as the gums. Thus, data processing apparatus 1 performs pattern matching between the one tooth indicated with the first three-dimensional data and the one tooth indicated with the second three-dimensional data using the crown portion that is hard tissue as a reference. More specifically, data processing apparatus 1 limits a target to be subjected to pattern matching to the crown portion that is hard tissue, that is, the crown portion enclosed as range F1 specified in the first three-dimensional data and the crown portion enclosed as range F2 specified in the second three-dimensional data. In a case where the crown portion enclosed as range F1 matches the crown portion enclosed as range F2 through such pattern matching, data processing apparatus 1 compares a shape of the soft tissue indicated with the first three-dimensional data and a shape of the soft tissue indicated with the second three-dimensional data regardless of whether or not the shapes of the pieces of the soft tissue match each other.

Data processing apparatus 1 extracts a difference for each point by comparing each point of a point cloud constituting the soft tissue indicated with the first three-dimensional data and each point of a point cloud constituting the soft tissue indicated with the second three-dimensional data. Specifically, data processing apparatus 1 sets a predetermined range R centered on each point for each of the points constituting the soft tissue indicated with the first three-dimensional data. Further, data processing apparatus 1 specifies from the second three-dimensional data, one point closest to one point in the first three-dimensional data among the points included in range R of one point of the first three-dimensional data and calculates a difference value (distance between two points) between the specified one point in the second three-dimensional data and the one point in the first three-dimensional data. Data processing apparatus 1 stores the calculated difference value of the shape in memory 12 or storage apparatus 13 in association with the three-dimensional data of the one point that has been compared in the second three-dimensional data. Data processing apparatus 1 performs such comparison for each of the points constituting the soft tissue indicated with each of the first three-dimensional data and the second three-dimensional data and stores a difference value of the shape at each point. Note that in a case where the three-dimensional data is mesh data, data processing apparatus 1 may calculate a difference value (distance between two points) between respective mesh vertices, may calculate a difference value (distance between a point and a plane) between the mesh vertex and the center of a mesh plane, or may calculate a difference value (distance between two planes) between centers of the respective mesh planes.

Further, data processing apparatus 1 can detect change in color of the soft tissue in addition to the shape of the soft tissue. For example, data processing apparatus 1 specifies from the second three-dimensional data, one point closest to one point of the first three-dimensional data among points included in range R of one point of the first three-dimensional data and calculates a difference in color (difference in hue, chroma or brightness) between the specified one point in the second three-dimensional data and the one point in the first three-dimensional data. Data processing apparatus 1 stores the calculated difference value in color in memory 12 or storage apparatus 13 in association with three-dimensional data of the one point that has been compared in the second three-dimensional data. Data processing apparatus 1 performs such comparison for each of the points constituting the soft tissue indicated with each of the first three-dimensional data and the second three-dimensional data and stores a difference value in color at each point.

Data processing apparatus 1 can detect change in the soft tissue in the whole row of teeth between the first timing and the second timing by performing the comparison as illustrated in FIG. 6C on each of a plurality of teeth included in the row of teeth. For example, as illustrated in FIG. 6C, in a case where the respective points constituting the soft tissue indicated with the second three-dimensional data are located on an outer side in the oral cavity than the respective points constituting the soft tissue indicated with the first three-dimensional data, data processing apparatus 1 can detect that the soft tissue has swollen during a period from the first timing to the second timing. On the other hand, in a case where the respective points constituting the soft tissue indicated with the second three-dimensional data are located on an inner side in the oral cavity than the respective points constituting the soft tissue indicated with the first three-dimensional data, data processing apparatus 1 can detect that the soft tissue has involuted during a period from the first timing to the second timing.

Further, in a case where the respective points constituting the soft tissue indicated with the second three-dimensional data are more reddish than the respective points constituting the soft tissue indicated with the first three-dimensional data, data processing apparatus 1 can detect that the soft tissue has swollen during a period from the first timing to the second timing.

Data processing apparatus 1 may predict change in the soft tissue in the future later than the second timing on the basis of the difference value calculated by comparison between the soft tissue indicated with the first three-dimensional data and the soft tissue indicated with the second three-dimensional data. For example, data processing apparatus 1 may predict a shape or a color of the soft tissue in the future using statistics processing on the basis of the calculated difference value and store a prediction result. In one embodiment, data processing apparatus 1 may predict a shape or a color of the soft tissue in the future using AI (trained estimation model) on the basis of the calculated difference value and store the prediction result.

In this manner, data processing apparatus 1 can compare the soft tissue corresponding to the tooth indicated with the first three-dimensional data and the soft tissue corresponding to the tooth indicated with the second three-dimensional data using a shape of a crown portion of the one tooth as a reference. This enables data processing apparatus 1 to detect change in a condition of the soft tissue with higher accuracy than simple comparison of the whole row of teeth by comparing the soft tissue indicated with the first three-dimensional data and the soft tissue indicated with the second three-dimensional data while limiting a portion to be compared to the soft tissue corresponding to one tooth. Further, data processing apparatus 1 can purely compare change in only the soft tissue by comparing the soft tissue indicated with the first three-dimensional data and the soft tissue indicated with the second three-dimensional data using a crown portion that is hard tissue whose shape is less likely to temporally change as a reference, so that it is possible to detect change in the condition of the soft tissue with higher accuracy than comparison using one tooth and the whole soft tissue corresponding to the tooth as a reference.

Example of Display of Comparison Result

Figure 7:
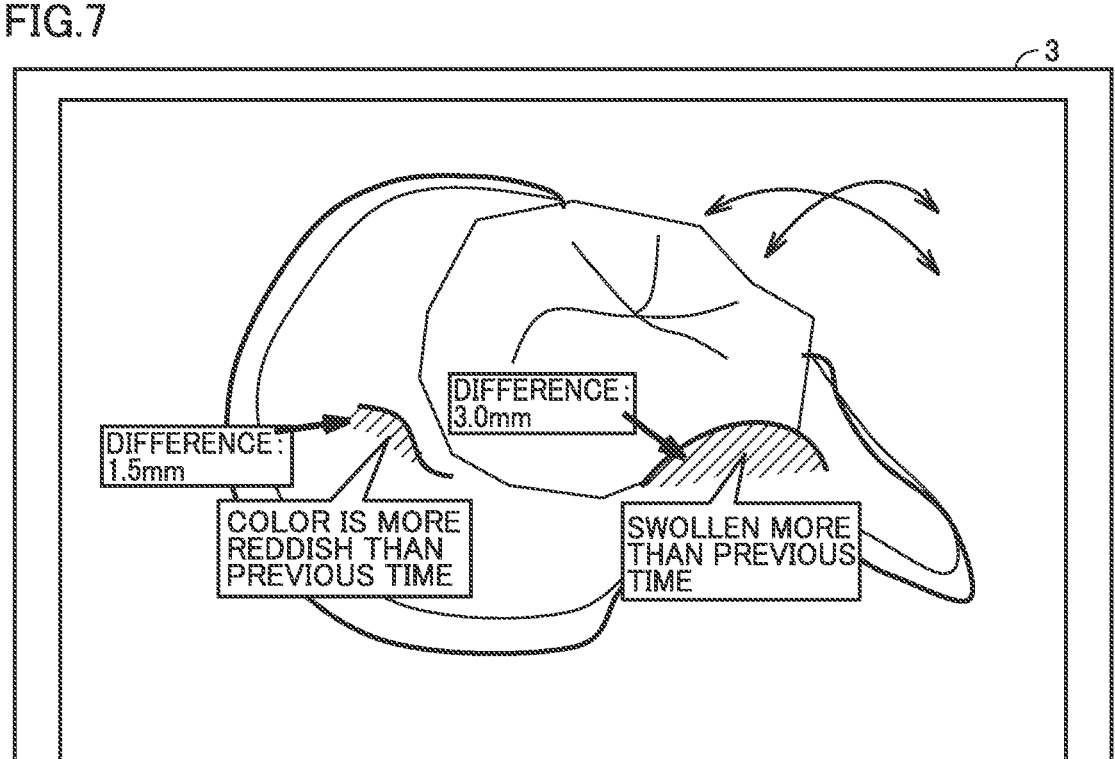
FIG. 7 is a view for explaining an example of display of a comparison result of the soft tissue to be executed by the data processing apparatus according to the first embodiment.

Display of a comparison result in the comparison processing to be executed by data processing apparatus 1 will be described with reference to FIG. 7. FIG. 7 is a view for explaining an example of display of a comparison result of the soft tissue to be executed by data processing apparatus 1 according to the first embodiment.

As illustrated in FIG. 7, data processing apparatus 1 displays comparison information regarding the comparison result of the soft tissue between the first three-dimensional data and the second three-dimensional data calculated through the comparison processing on display 3. For example, data processing apparatus 1 generates a rendering image indicating one tooth and soft tissue corresponding to the tooth at the first timing on the basis of the first three-dimensional data and generates a rendering image indicating the one tooth and the soft tissue corresponding to the tooth at the second timing on the basis of the second three-dimensional data. Data processing apparatus 1 displays the generated two rendering images on display 3 in a superimposed manner. In this event, data processing apparatus 1 superimposes the two rendering images while aligning the crown portion indicated with the first three-dimensional data with the crown portion indicated with the second three-dimensional data. This enables data processing apparatus 1 to display a degree of change in shape and color of the soft tissue between the first three-dimensional data and the second three-dimensional data on display 3.

Further, data processing apparatus 1 may indicate the one tooth and the soft tissue corresponding to the tooth indicated with the first three-dimensional data and the one tooth and the soft tissue corresponding to the tooth indicated with the second three-dimensional data in colors different from each other. For example, data processing apparatus 1 may indicate the one tooth and the soft tissue corresponding to the tooth indicated with the first three-dimensional data in blue and indicates the one tooth and the soft tissue corresponding to the tooth indicated with second three-dimensional data in red.

Data processing apparatus 1 may display, on display 3, a numerical value corresponding to the comparison result between the soft tissue indicated with the first three-dimensional data and the soft tissue indicated with the second three-dimensional data for a portion designated by the user moving a cursor on a screen of display 3 using mouse 5. For example, in an example in FIG. 7, data processing apparatus 1 displays, on display 3, a difference value corresponding to a portion of the soft tissue, such as "difference: 1.5 mm" or "difference: 3.0 mm" as a difference value of a shape between the soft tissue indicated with the first three-dimensional data and the soft tissue indicated with the second three-dimensional data.

Data processing apparatus 1 may highlight and display a portion for which the difference value is a predetermined value or more. For example, data processing apparatus 1 may highlight and display the portion for which the difference value is the predetermined value or more using color, blinking, a symbol (for example, a flag mark), or the like.

Data processing apparatus 1 may highlight and display the portion for which the difference value is the predetermined value or more using a color in accordance with the difference value, or the like. For example, data processing apparatus 1 may indicate a portion of the swollen soft tissue and a portion of the involuted soft tissue during a period from the first timing to the second timing in colors different from each other. Further, data processing apparatus 1 may indicate the portion of the swollen soft tissue in colors different in accordance with a degree of swelling of the soft tissue. Still further, data processing apparatus 1 may indicate the portion of the involuted soft tissue in colors different in accordance with a degree of involution of the soft tissue.

Data processing apparatus 1 may display, on display 3, a comment regarding the comparison result (change) in the shape between the soft tissue indicated with the first three-dimensional data and the soft tissue indicated with the second three-dimensional data for a portion designated by the user moving the cursor on the screen of display 3 using mouse 5. For example, in the example in FIG. 7, data processing apparatus 1 displays a comment of "swollen more than the previous time" on display 3.

Data processing apparatus 1 may display, on display 3, a comment regarding the comparison result (change) in a color between the soft tissue indicated with the first three-dimensional data and the soft tissue indicated with the second three-dimensional data for a portion designated by the user moving the cursor on the screen of display 3 using mouse 5. For example, in the example in FIG. 7, data processing apparatus 1 displays a comment of "color is more reddish than the previous time" on display 3.

Data processing apparatus 1 may predict a shape or a color of the soft tissue in the future later than the second timing on the basis of the difference value calculated by comparison between the soft tissue indicated with the first three-dimensional data and the soft tissue indicated with the second three-dimensional data using statistical processing and AI and may display the prediction result on display 3.

Note that data processing apparatus 1 may perform all or one of the display of the comparison information described above using FIG. 7. Data processing apparatus 1 only needs to perform at least one of the display of above-described comparison information. Data processing apparatus 1 may display the comment as in the example in FIG. 7 for a portion with a great difference value on display 3 without the user using mouse 5.

In this manner, data processing apparatus 1 can convey the comparison result of the shape or color between the soft tissue indicated with the first three-dimensional data and the soft tissue indicated with the second three-dimensional data to the user in an easy-to-understand manner. Further, data processing apparatus 1 displays the comment regarding the comparison result, highlighting in accordance with the comparison result, prediction of change in the soft tissue based on the comparison result, and the like, on display 3, as well as the numerical value corresponding to the comparison result of the shape, and thus, data processing apparatus 1 can convey the comparison result to the user in an easy-to-understand manner, so that, it is, for example, possible to bring attention to swelling or involution of the gums and encourage prevention.

Flow of Comparison Processing

A flow of the comparison processing of the soft tissue to be executed by data processing apparatus 1 will be described with reference to FIG. 8. FIG. 8 is a flowchart of the comparison processing of the soft tissue to be executed by data processing apparatus 1 according to the first embodiment. Data processing apparatus 1 (calculation apparatus 11) can execute the comparison processing indicated in FIG. 8 by executing data processing program 100. Note that in FIG. 8, "S" is used as an abbreviation of "STEP".

As indicated in FIG. 8, data processing apparatus 1 acquires the first three-dimensional data and the second three-dimensional data (S1). For example, data processing apparatus 1 stores the first three-dimensional data acquired at the first timing in memory 12 or storage apparatus 13, stores the second three-dimensional data acquired at the second timing in memory 12 or storage apparatus 13 and acquires the stored first three-dimensional data and second three-dimensional data from memory 12 or storage apparatus 13 in S1.

Data processing apparatus 1 designates one tooth from a row of teeth indicated in each of the first three-dimensional data and the second three-dimensional data (S2). For example, as illustrated in FIG. 5A, data processing apparatus 1 sets the designated point P for one tooth from a plurality of teeth included in the row of teeth in accordance with designation by the user.

Data processing apparatus 1 extracts three-dimensional data of a portion corresponding to the tooth designated in S2 from each of the first three-dimensional data and the second three-dimensional data (S3). For example, as illustrated in FIG. 5A, data processing apparatus 1 extracts three-dimensional data of a portion enclosed as predetermined range Q including designated point P set for one tooth. This enables data processing apparatus 1 to extract three-dimensional data of the one tooth designated by the user and the soft tissue corresponding to the tooth.

As illustrated in FIGS. 6A-6C, data processing apparatus 1 performs alignment using a shape of a crown portion of the designated one tooth as a reference and compares the soft tissue around the tooth (predetermined range of the soft tissue that contacts the tooth) between the first three-dimensional data and the second three-dimensional data (S4). In this event, in a case where the crown portion of the tooth indicated with the first three-dimensional data cannot be aligned with the crown portion of the tooth indicated with the second three-dimensional data because a shape of the crown portion of the designated one tooth cannot be specified due to dental therapy, loss, or the like, data processing apparatus 1 may display an error screen on display 3. In one embodiment, the processing may transition to the processing in S2, and data processing apparatus 1 may designate a tooth that is to be used as the reference next.

Data processing apparatus 1 stores the comparison result in S4 in memory 12 or storage apparatus 13 (S5). Data processing apparatus 1 outputs comparison information corresponding to the comparison result in S4 (S6). For example, as illustrated in FIG. 7, data processing apparatus 1 displays an image corresponding to the comparison result, a numerical value corresponding to the comparison result, a comment regarding the comparison result, information regarding prediction of change in the soft tissue based on the comparison result, and the like on display 3 as the comparison information. Note that data processing apparatus 1 may transmit the comparison information corresponding to the comparison result to a hospital server or a server outside a hospital (for example, a cloud server) via communication apparatus 18. Then, data processing apparatus 1 ends the present processing flow.

In this manner, data processing apparatus 1 can compare the soft tissue between the first three-dimensional data and the second three-dimensional data acquired at different timings while limiting the portion to be compared to the soft tissue corresponding to the designated tooth and can output the comparison result. This enables data processing apparatus 1 to detect change in the condition of the soft tissue with higher accuracy than simple comparison of the whole row of teeth by comparing the soft tissue indicated with the first three-dimensional data and the soft tissue indicated with the second three-dimensional data while limiting the portion to be compared to the soft tissue corresponding to the designated tooth.

Note that data processing apparatus 1 may execute the processing from S3 to S6 while designating the tooth in S2 in accordance with predetermined order set in advance by the user and may repeatedly execute the processing from S2 to S6 until all the teeth included in the row of teeth are designated and comparison information is output for all the teeth. Data processing apparatus 1 can detect temporal change in the soft tissue for the teeth in the whole row of teeth by executing the comparison processing indicated in FIG. 8 on all the teeth.

Second Embodiment

Data processing apparatus 1 according to a second embodiment of the present disclosure will be described in detail with reference to FIGS. 9A-9C. Note that only portions different from data processing apparatus 1 according to the first embodiment will be described in data processing apparatus 1 according to the second embodiment, the same reference numerals will be assigned to the portions that are the same as those in data processing apparatus 1 according to the first embodiment, and redundant description will be omitted.

FIGS. 9A-9C illustrate a view for explaining an example of comparison of the soft tissue to be executed by data processing apparatus 1 according to the second embodiment. As illustrated in FIGS. 9A-9C, data processing apparatus 1 may generate two-dimensional images including an occlusal surface of at least one tooth on the basis of the first three-dimensional data and the second three-dimensional data and compare the pieces of the soft tissue using a shape of a crown portion as a reference using the two-dimensional images.

For example, data processing apparatus 1 generates a two-dimensional image of a crown portion in a case where the crown portion of the one tooth indicated with the first three-dimensional data is viewed from an occlusal surface direction on the basis of the first three-dimensional data. In a similar manner, data processing apparatus 1 generates a two-dimensional image of a crown portion in a case where the crown portion of the one tooth indicated with the second three-dimensional data is viewed from an occlusal surface direction on the basis of the second three-dimensional data. Data processing apparatus 1 superimposes the one tooth and the soft tissue indicated with the first three-dimensional data on the tooth and the soft tissue indicated with the second three-dimensional data so that the crown portion indicated with the two-dimensional image generated on the basis of the first three-dimensional data is aligned with the crown portion indicated with the two-dimensional image generated on the basis of the second three-dimensional data. This enables data processing apparatus 1 to purely compare the soft tissue indicated with the first three-dimensional data and the soft tissue indicated with the second three-dimensional data using the crown portion indicated with the first three-dimensional data and the crown portion indicated with the second three-dimensional data as a reference.

This enables data processing apparatus 1 to compare the soft tissue between the first three-dimensional data and the second three-dimensional data using a shape of the crown portion as a reference after clarifying the shape of the crown portion that is less likely to temporally change, so that it is possible to detect change in the condition of the soft tissue with high accuracy.

Third Embodiment

Data processing apparatus 1 according to a third embodiment of the present disclosure will be described in detail with reference to FIGS. 10A-10C. Note that only portions different from data processing apparatus 1 according to the first embodiment will be described in data processing apparatus 1 according to the third embodiment, the same reference numerals will be assigned to portions that are the same as those in data processing apparatus 1 according to the first embodiment, and redundant description will be omitted.

FIGS. 10A-10C illustrate a view for explaining extraction of three-dimensional data that is to be subjected to comparison processing according to the third embodiment. As illustrated in FIGS. 5A-5B, data processing apparatus 1 according to the first embodiment is configured to specify one tooth from the plurality of teeth included in the row of teeth indicated with the three-dimensional data and extract three-dimensional data of the tooth and soft tissue corresponding to the tooth. In contrast, as illustrated in FIGS. 10A-10C, data processing apparatus 1 according to the third embodiment is configured to specify two adjacent teeth from the plurality of teeth included in the row of teeth indicated with the three-dimensional data and extract three-dimensional data of the two teeth and soft tissue corresponding to the two teeth.

Specifically, as illustrated in FIG. 10A, data processing apparatus 1 designates a boundary portion of the two adjacent teeth for which the three-dimensional data is to be extracted among the plurality of teeth included in the row of teeth as designated point P. Then, as illustrated in FIG. 10B, data processing apparatus 1 extracts three-dimensional data of the two teeth and the soft tissue corresponding to the two teeth enclosed as predetermined range Q including designated point P. Then, as illustrated in FIG. 10C, data processing apparatus 1 extracts three-dimensional data for each of two adjacent teeth while switching a portion for which the three-dimensional data is to be extracted by moving a position of designated point P along the row of teeth.

In this manner, data processing apparatus 1 is configured to extract three-dimensional data for each of two adjacent teeth in a manner such that data processing apparatus 1 sets designated point P between a first tooth and a second tooth that is adjacent to the first tooth, extracts three-dimensional data for a set of the first tooth and the second tooth, then sets designated point P between a third tooth that is adjacent to the second tooth and a fourth tooth that is adjacent to the third tooth and extracts three-dimensional data for a set of the third tooth and the fourth tooth.

Note that data processing apparatus 1 may be configured to extract three-dimensional data for each of two adjacent teeth and extract three-dimensional data while one of the two teeth is overlapped in a manner such that data processing apparatus 1 sets designated point P between the first tooth and the second tooth that is adjacent to the first tooth, extracts three-dimensional data for a set of the first tooth and the second tooth, then sets designated point P between the second tooth and the third tooth that is adjacent to the second tooth and extracts three-dimensional data for a set of the second tooth and the third tooth. In other words, data processing apparatus 1 may extract three-dimensional data for each of two adjacent teeth while sequentially switching teeth to be designated as designated point P along the tooth row direction.

Data processing apparatus 1 may detect temporal change in the soft tissue corresponding to the two adjacent teeth using crown portions of the two adjacent teeth as a reference using the three-dimensional data of the two adjacent teeth extracted as described above. Note that data processing apparatus 1 may compare the soft tissue corresponding to the two adjacent teeth between the first timing and the second timing using a set of all of the crown portions of the two adjacent teeth as a reference, may compare the soft tissue corresponding to the two adjacent teeth between the first timing and the second timing using each of the crown portions of the two adjacent teeth as a reference, or may compare the soft tissue corresponding to the two adjacent teeth between the first timing and the second timing using one of the crown portions of the two adjacent teeth as a reference.

This enables data processing apparatus 1 according to the third embodiment to detect temporal change in the soft tissue for each of two adjacent teeth, so that it is possible to shorten a period required for comparison processing compared to a case where temporal change in the soft tissue is detected for each tooth. Further, data processing apparatus 1 can detect change in a wider range such as soft tissue around an adjacent portion of two teeth than change in the soft tissue for each tooth.

Fourth Embodiment

Data processing apparatus 1 according to a fourth embodiment of the present disclosure will be described in detail with reference to FIGS. 11A-11C. Note that only portions different from data processing apparatus 1 according to the first embodiment will be described in data processing apparatus 1 according to the fourth embodiment, the same reference numerals will be assigned to portions that are the same as those in data processing apparatus 1 according to the first embodiment, and redundant description will be omitted.

FIGS. 11A-11C illustrate a view for explaining extraction of three-dimensional data that is to be subjected to comparison processing according to the fourth embodiment. As illustrated in FIGS. 11A-11C, data processing apparatus 1 according to the fourth embodiment is configured to specify three adjacent teeth from the plurality of teeth included in the row of teeth indicated with the three-dimensional data and extract three-dimensional data of the three teeth and soft tissue corresponding to the three teeth.

Specifically, as illustrated in FIG. 11A, data processing apparatus 1 designates a tooth at the center of three adjacent teeth for which three-dimensional data is to be extracted as designated point P among the plurality of teeth included in the row of teeth. Then, as illustrated in FIG. 11B, data processing apparatus 1 extracts three-dimensional data of the three teeth and soft tissue corresponding to the three teeth enclosed as predetermined range Q including designated point P. Then, as illustrated in FIG. 11C, data processing apparatus 1 extracts three-dimensional data for each of adjacent three teeth while switching a portion for which the three-dimensional data is to be extracted by moving the position of designated point P along the row of teeth.

In this manner, data processing apparatus 1 is configured to extract three-dimensional data for each of three adjacent teeth in a manner such that data processing apparatus 1 sets designated point P at the second tooth among the first tooth, the second tooth that is adjacent to the first tooth and the third tooth that is adjacent to the second tooth, extracts three-dimensional data for a set of the first tooth, the second tooth and the third tooth, then, sets designated point P at a fifth tooth among a fourth tooth that is adjacent to the third tooth, the fifth tooth that is adjacent to the fourth tooth and a sixth tooth that is adjacent to the fifth tooth and extracts three-dimensional data for a set of the fourth tooth, the fifth tooth and the sixth tooth.

Note that data processing apparatus 1 may be configured to extract three-dimensional data for each of three adjacent teeth and extract three-dimensional data while one of the three teeth is overlapped in a manner such that data processing apparatus 1 sets designated point P at the second tooth among the first tooth, the second tooth that is adjacent to the first tooth and the third tooth that is adjacent to the second tooth, extracts three-dimensional data for a set of the first tooth, the second tooth and the third tooth, then, sets designated point P at the third tooth among the second tooth, the third tooth and the fourth tooth that is adjacent to the third tooth and extracts three-dimensional data for a set of the second tooth, the third tooth and the fourth tooth. In other words, data processing apparatus 1 may extract three-dimensional data for each of three adjacent teeth while sequentially switching the tooth to be designated as designated point P along the tooth row direction.

Data processing apparatus 1 may detect temporal change in the soft tissue corresponding to the three adjacent teeth using crown portions of the three adjacent teeth as a reference using the three-dimensional data of the three adjacent teeth extracted as described above. Note that data processing apparatus 1 may compare the soft tissue corresponding to the three adjacent teeth between the first timing and the second timing using a set of all the crown portions of the three adjacent teeth as a reference, may compare the soft tissue corresponding to the three adjacent teeth between the first timing and the second timing using each of the crown portions of the three adjacent teeth as a reference or may compare the soft tissue corresponding to the three adjacent teeth between the first timing and the second timing using one of the crown portions of the three adjacent teeth as a reference.

This enables data processing apparatus 1 according to the fourth embodiment to detect temporal change in the soft tissue for each of three adjacent teeth, so that it is possible to shorten a period required for comparison processing than a case where temporal change in the soft tissue is detected for each tooth or each of two teeth. Further, data processing apparatus 1 can detect change in a wider range than change in the soft tissue for each tooth or each of two teeth.

Note that data processing apparatus 1 may extract three-dimensional data for each of four or more adjacent teeth and may detect temporal change in the soft tissue for each of four or more adjacent teeth. Further, data processing apparatus 1 may extract three-dimensional data for each of one and half teeth and detect temporal change in the soft tissue for each of one and half teeth. For example, data processing apparatus 1 may extract three-dimensional data for each of one and half teeth in a manner such that data processing apparatus 1 sets designated point P between the first tooth and the second tooth that is adjacent to the first tooth, extracts three-dimensional data for a set of the first tooth and half of the second tooth closer to the first tooth, then sets designated point P between the second tooth and the third tooth that is adjacent to the second tooth and extracts three-dimensional data for a set of the remaining half of the second tooth farther from the first tooth and the third tooth.

Fifth Embodiment

Data processing apparatus 1 according to a fifth embodiment of the present disclosure will be described in detail with reference to FIGS. 12A-12C and FIG. 13. Note that only portions different from data processing apparatus 1 according to the first embodiment will be described in data processing apparatus 1 according to the fifth embodiment, the same reference numerals will be assigned to portions that are the same as those in data processing apparatus 1 according to the first embodiment, and redundant description will be omitted.

Figures 12A, 12B, 12C:
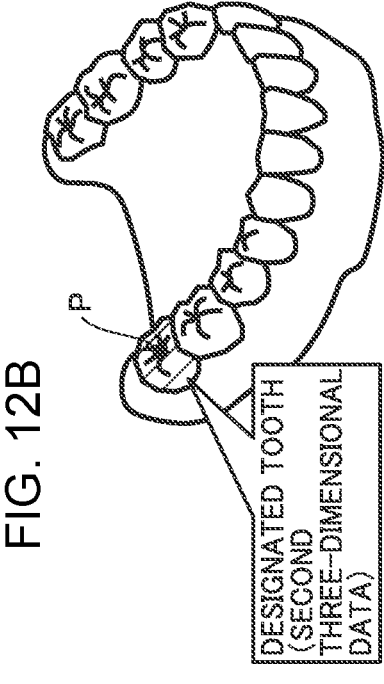
FIG. 12A is a view for explaining extraction of three-dimensional data to be subjected to comparison processing according to a fifth embodiment.
FIG. 12B is a view for explaining extraction of three-dimensional data to be subjected to comparison processing according to a fifth embodiment.
FIG. 12C is a view for explaining extraction of three-dimensional data to be subjected to comparison processing according to a fifth embodiment.

FIGS. 12A-12C illustrate a view for explaining extraction of three-dimensional data to be subjected to comparison processing according to the fifth embodiment. As illustrated in FIGS. 5A-5B, FIGS. 10A-10C and FIGS. 11A-11C, data processing apparatus 1 according to the first to the fourth embodiments are configured to extract three-dimensional data of at least one tooth and the soft tissue corresponding to the at least one tooth by dividing and cutting the row of teeth indicated with the three-dimensional data for each of the at least one tooth. In contrast, as illustrated in FIGS. 12A-12C, data processing apparatus 1 according to the fifth embodiment is configured to extract three-dimensional data of at least one tooth and the soft tissue corresponding to the at least one tooth while maintaining a shape of the row of teeth without dividing and cutting the row of teeth indicated with the three-dimensional data.

Specifically, as illustrated in FIG. 12A, data processing apparatus 1 designates one tooth as designated point P among the plurality of teeth indicated with the first three-dimensional data acquired at the first timing. As illustrated in FIG. 12B, data processing apparatus 1 designates one tooth as designated point P among the plurality of teeth indicated with the second three-dimensional data acquired at the second timing. The same tooth is designated between the first three-dimensional data and the second three-dimensional data.

Data processing apparatus 1 compares soft tissue corresponding to the tooth indicated with the first three-dimensional data and soft tissue corresponding to the tooth indicated with the second three-dimensional data using a crown portion of the tooth designated in the first three-dimensional data and a crown portion of the tooth designated in the second three-dimensional data as a reference. Specifically, as illustrated in FIG. 12C, data processing apparatus 1 superimposes the whole row of teeth indicated with the first three-dimensional data on the whole row of teeth indicated with the second three-dimensional data while aligning the crown portion of the tooth designated in the first three-dimensional data with the crown portion of the tooth designated in the second three-dimensional data. Then, data processing apparatus 1 compares the soft tissue between the first three-dimensional data and the second three-dimensional data at a portion enclosed as range Q including designated point P. In this manner, data processing apparatus 1 according to the fifth embodiment is configured to superimpose the whole row of teeth indicated with the first three-dimensional data on the whole row of teeth indicated with the second three-dimensional data instead of dividing and cutting the row of teeth indicated with the three-dimensional data for each of at least one tooth as in data processing apparatus 1 according to the first to the fourth embodiments and compare the first three-dimensional data and the second three-dimensional data for the tooth designated as designated point P and the soft tissue corresponding to the tooth.

As described above, data processing apparatus 1 compares the soft tissue corresponding to one tooth indicated with the first three-dimensional data and the soft tissue corresponding to the one tooth indicated with the second three-dimensional data using the designated one tooth as a reference, records the comparison result, and then switches a tooth that becomes a reference for comparison processing by designating one tooth adjacent to the tooth as designated point P. By switching a tooth to be designated as designated point P along the row of teeth in this manner, data processing apparatus 1 can execute comparison processing for soft tissue corresponding to each tooth using each of the plurality of teeth included in the row of teeth as a reference. Note that data processing apparatus 1 does not execute comparison processing at the same time for a tooth to be compared and a tooth at a position farther from a position of the tooth to be compared in the tooth row direction (for example, a tooth five teeth away from the tooth to be compared). This is because as a distance becomes greater in the tooth row direction, an error is more likely to occur between a position of the tooth indicated with the three-dimensional data and an actual position of the tooth.

Note that data processing apparatus 1 may designate the tooth that becomes a reference as designated point P in accordance with designation by the user. Data processing apparatus 1 may designate the tooth that becomes a reference as designated point P in predetermined order set in advance by the user. Data processing apparatus 1 may automatically switch the tooth to be designated as designated point P every time a predetermined period elapses. Data processing apparatus 1 may randomly designate the tooth that becomes a reference as designated point P not limited to sequentially designating the tooth that becomes a reference as designated point P along the row of teeth.

While data processing apparatus 1 superimposes the whole row of teeth indicated with the first three-dimensional data on the whole row of teeth indicated with the second three-dimensional data using the designated tooth as a reference in this manner, data processing apparatus 1 limits the soft tissue to be compared to soft tissue corresponding to the designated tooth (soft tissue around the designated tooth). This enables data processing apparatus 1 to detect change in the condition of the soft tissue with higher accuracy than a case where the whole row of teeth is simply compared between the first three-dimensional data and the second three-dimensional data.

FIG. 13 is a flowchart of the comparison processing of the soft tissue to be executed by data processing apparatus 1 according to the fifth embodiment. Data processing apparatus 1 (calculation apparatus 11) can execute the comparison processing indicated in FIG. 13 by executing data processing program 100. Note that in FIG. 13, "S" is used as an abbreviation of "STEP".

As indicated in FIG. 13, data processing apparatus 1 acquires the first three-dimensional data and the second three-dimensional data (S11). For example, data processing apparatus 1 stores the first three-dimensional data acquired at the first timing in memory 12 or storage apparatus 13, stores the second three-dimensional data acquired at the second timing in memory 12 or storage apparatus 13 and acquires the stored first three-dimensional data and second three-dimensional data from memory 12 or storage apparatus 13 in S11.

Data processing apparatus 1 designates one tooth among the row of teeth indicated with each of the first three-dimensional data and the second three-dimensional data (S12). For example, as illustrated in FIG. 12A and FIG. 12B, data processing apparatus 1 sets one tooth among the plurality of teeth included in the row of teeth as designated point P in accordance with designation by the user.

As illustrated in FIG. 12C, data processing apparatus 1 performs alignment using a shape of a crown portion of the designated one tooth as a reference, superimposes the whole row of teeth indicated with the first three-dimensional data on the whole row of teeth indicated with the second three-dimensional data and compares pieces of soft tissue around the designated tooth (predetermined range of the soft tissue that contacts the tooth) between the first three-dimensional data and the second three-dimensional data (S13). In this event, in a case where the crown portion of the tooth indicated with the first three-dimensional data cannot be aligned with the crown portion of the tooth indicated with the second three-dimensional data because a shape of the crown portion of the designated tooth cannot be specified due to dental therapy, loss, or the like, data processing apparatus 1 may display an error screen on display 3. In one embodiment, the processing may transition to S12, and data processing apparatus 1 may designate a tooth that is to be used as the reference next.

Data processing apparatus 1 stores the comparison result in S13 in memory 12 or storage apparatus 13 (S14). Data processing apparatus 1 outputs comparison information corresponding to the comparison result in S14 (S15). Data processing apparatus 1 determines whether or not all the teeth included in the row of teeth are designated (S16). In a case where all the teeth are not designated (S16: No), the processing transitions to S12, and data processing apparatus 1 designates the next tooth. On the other hand, in a case where all the teeth are designated (S16: Yes), data processing apparatus 1 ends the present processing flow.

In this manner, data processing apparatus 1 can compare the pieces of the soft tissue between the first three-dimensional data and the second three-dimensional data acquired at different timings while limiting the portion to be compared to the soft tissue corresponding to the designated tooth and output the comparison result. This enables data processing apparatus 1 to detect change in the condition of the soft tissue with higher accuracy than simple comparison of the whole row of teeth by comparing the soft tissue indicated with the first three-dimensional data and the soft tissue indicated with the second three-dimensional data while limiting the portion to be compared to the soft tissue corresponding to the designated tooth.

Note that in a case where data processing apparatus 1 designates the tooth that becomes a reference as designated point P in accordance with designation by the user, data processing apparatus 1 may make an inquiry, to the user, as to whether or not the user designates the tooth using icon display, or the like, in the processing in S16. In this case, in a case where the user designates the tooth that is to be used as the reference next, the processing may transition to S12, and in a case where the user does not designate the tooth that is to be used as the reference next, the present processing flow may end.

Modifications

The present disclosure is not limited to the above-described embodiments, and various modifications and applications are further possible. Modifications that are applicable to the present disclosure will be described below.

Data processing apparatus 1 according to the above-described embodiments are configured to detect change in the soft tissue between two timings such as the first timing and the second timing which are different from each other. In contrast, data processing apparatus 1 according to the modification may be configured to detect change in the soft tissue among three or more timings different from one another not limited to two timings different from each other. For example, data processing apparatus 1 may compare pieces of the soft tissue between the first three-dimensional data acquired at the first timing and the second three-dimensional data acquired at the second timing after the first timing, store the comparison result, and then compare pieces of the soft tissue between the second three-dimensional data acquired at the second timing and third three-dimensional data acquired at a third timing after the second timing and store the comparison result. In this manner, data processing apparatus 1 may compare the pieces of the soft tissue at three or more timings different from one another and display change in the soft tissue among the three or more timings on display 3, or the like. This enables the user to, for example, record and see temporal change in the soft tissue for a plurality of years in the past.

Data processing apparatus 1 according to the above-described embodiments is configured to detect change in the soft tissue using IOS data including position information of each point of a point cloud representing surfaces of objects inside the oral cavity. In contrast, data processing apparatus 1 according to the modification may be configured to detect change in the soft tissue using optical coherence tomography (OCT) data including optical coherence tomography information of the objects inside the oral cavity. See Japanese Patent No. 5642114 for details of the OCT data. Data processing apparatus 1 acquires OCT data including the optical coherence tomography information of the objects inside the oral cavity from an OCT apparatus such as a time domain OCT (TD-OCT), a spectral domain OCT (SD-OCT) and a swept source OCT (SS-OCT), as the first three-dimensional data and the second three-dimensional data. Data processing apparatus 1 may compare the soft tissue around at least one tooth (predetermined range of the soft tissue that contacts the tooth) between the first three-dimensional data and the second three-dimensional data using a shape of a crown portion of the at least one tooth included in the objects indicated with the OCT data as a reference.

Data processing apparatus 1 according to the modification may further include an input interface to which fluorescence color data is input, the fluorescence color data including information of fluorescence colors emitted by the objects when the objects are irradiated with excitation light. In the dental field, in a case where teeth (crown portions) or soft tissue inside the oral cavity are irradiated with excitation light using a light emitting diode (LED), or the like, it is known that a disease such as a cavity or a malignant tumor can be found on the basis of a fluorescence color emitted by the irradiated portion. Thus, data processing apparatus 1 can determine whether or not there is a disease at the objects inside the oral cavity by acquiring first fluorescence color data including information on fluorescence colors emitted by the objects when the objects inside the oral cavity are irradiated with excitation light at a first timing and second fluorescence color data including information on fluorescence colors emitted by the objects when the objects inside the oral cavity are irradiated with excitation light at a second timing after the first timing and comparing the first fluorescence color data and the second fluorescence color data. Data processing apparatus 1 may output comparison information indicating a comparison result between the first fluorescence color data and the second fluorescence color data to display 3, a server apparatus, or the like.

Data processing apparatus 1 may be a cloud type server apparatus. In other words, calculation apparatus 11 (calculation unit) may have a function as a computer (a processor, a processing circuitry) at the cloud type server apparatus. For example, data processing apparatus 1 may be configured to be able to perform communication with a user terminal such as a smartphone possessed by the user or the subject. Data processing apparatus 1 may acquire the three-dimensional data acquired by three-dimensional scanner 2 and output output data including comparison information detected on the basis of the three-dimensional data to the user terminal. The user terminal, which can perform communication with data processing apparatus 1 by starting an application downloaded in advance, may acquire the comparison information and display the comparison information on a display on the basis of the output data received from data processing apparatus 1. Further, data processing apparatus 1 itself may be the user terminal such as a smartphone described above.

It should be understood that the embodiments disclosed herein are by way of illustration and example only and are not to be taken by way of limitation. The scope of the present disclosure is not indicated by the above description but indicated by the claims and is intended to include all changes within the content and the range equivalent to the claims. Note that the components exemplified in the present embodiments and the components exemplified in the modifications can be combined as appropriate.

What is claimed is:

1. A data processing apparatus that processes three-dimensional data of objects inside an oral cavity, the data processing apparatus comprising:
   input interface circuitry to which first three-dimensional data and second three-dimensional data indicating including position information of each point of a point cloud representing surfaces of at least one tooth and gums around the at least one tooth included in the objects acquired at timings different from each other for a same person are input; and
   processing circuitry configured to compare the gums around the at least one tooth between the first three-dimensional data and the second three-dimensional data using a shape of a crown portion of the at least one tooth included as a reference and output comparison information regarding a comparison result,
   wherein the processing is circuitry configured to compare each point of a point cloud comprising the gums around the at least one tooth indicated by the first three-dimensional data with each point of a point cloud comprising the gums around the at least one tooth indicated by the second three-dimensional data.

2. The data processing apparatus according to claim 1, wherein the processing circuitry is configured to compare the gums of the at least one tooth using a shape of a whole or a predetermined range of the crown portion of the at least one tooth as a reference.

3. The data processing apparatus according to claim 1, wherein the processing circuitry is configured to extract the at least one tooth on a basis of a tooth designated by a user or a tooth selected in predetermined order.

4. The data processing apparatus according to claim 1, wherein the processing circuitry is configured to extract the at least one tooth and divide a row of teeth in a direction substantially orthogonal to a tooth row direction of an arch of the teeth.

5. The data processing apparatus according to claim 1, wherein the processing circuitry is configured to generate two-dimensional images including an occlusal surface of the at least one tooth on a basis of the first three-dimensional data and the second three-dimensional data and compare the gums using the shape of the crown portion as a reference using the two-dimensional images.

6. The data processing apparatus according to claim 1, wherein the comparison result includes a comparison result of a shape or a color of the gums.

7. The data processing apparatus according to claim 1, wherein the comparison information includes at least one of image data corresponding to the comparison result, a numerical value corresponding to the comparison result, a comment regarding the comparison result, and information regarding prediction of change in the gums based on the comparison result.

8. The data processing apparatus according to claim 1, wherein the first three-dimensional data and the second three-dimensional data include at least one of intra-oral scanner (IOS) data including position information of each point of a point cloud representing surfaces of the objects.

9. The data processing apparatus according to claim 1, wherein when the objects are irradiated with excitation light at timings different from each other, first fluorescence color data and second fluorescence color data including information of fluorescence colors emitted by the objects are further input to the input interface circuitry, and
   the processing circuitry is configured to compare the first fluorescence color data and the second fluorescence color data and output the comparison result as the comparison information.

10. A data processing method for processing three-dimensional data of objects inside an oral cavity by a computer, the data processing method comprising:
   acquiring, by processing circuitry of the computer, first three-dimensional data and second three-dimensional data including position information of each point of a point cloud representing surfaces of at least one tooth and gums around the at least one tooth included in the objects acquired at timings different from each other for a same person;
   comparing, by the processing circuitry of the computer, the gums around the at least one tooth between the first three-dimensional data and the second three-dimensional data using a shape of a crown portion of the at least one tooth included in as a reference; and
   outputting, by the processing circuitry of the computer, comparison information regarding a comparison result,
   wherein the data processing method further comprises comparing each point of a point cloud comprising the gums around the at least one tooth indicated by the first three-dimensional data with each point of a point cloud comprising the gums around the at least one tooth indicated by the second three-dimensional data.

11. The data processing method according to claim 10, wherein comparing the gums of the at least one tooth includes using a shape of a whole or a predetermined range of the crown portion of the at least one tooth as a reference.

12. The data processing method according to claim 10, further comprising extracting the at least one tooth on a basis of a tooth designated by a user or a tooth selected in predetermined order.

13. The data processing method according to claim 10, further comprising extracting the at least one tooth and dividing a row of teeth in a direction substantially orthogonal to a tooth row direction of an arch of the teeth.

14. The data processing method according to claim 10, further comprising generating two-dimensional images including an occlusal surface of the at least one tooth on a basis of the first three-dimensional data and the second three-dimensional data and comparing the gums using the shape of the crown portion as a reference using the two-dimensional images.

15. The data processing method according to claim 10, wherein the comparison result includes a comparison result of a shape or a color of the gums.

16. The data processing method according to claim 10, wherein the comparison information includes at least one of image data corresponding to the comparison result, a numerical value corresponding to the comparison result, a comment regarding the comparison result, and information regarding prediction of change in the gums based on the comparison result.

17. The data processing method according to claim 10, wherein the first three-dimensional data and the second three-dimensional data include at least one of intra-oral scanner (IOS) data including position information of each point of a point cloud representing surfaces of the objects.

18. A data processing system that processes three-dimensional data of objects inside an oral cavity, the data processing system comprising:

a three-dimensional scanner that acquires the three-dimensional data of the objects; and a data processing apparatus that processes the three-dimensional data acquired by the three-dimensional scanner, wherein the data processing apparatus comprises:

input interface circuitry to which first three-dimensional data and second three-dimensional data indicating including position information of each point of a point cloud representing surfaces of at least one tooth and gums around the at least one tooth included in the objects acquired at timings different from each other for a same person are input; and processing circuitry configured to compare the gums around the at least one tooth between the first three-dimensional data and the second three-dimensional data using a shape of a crown portion of the at least one tooth included as a reference and output comparison information regarding a comparison result, wherein the processing circuitry is configured to compare each point of a point cloud comprising the gums around the at least one tooth indicated by the first three-dimensional data with each point of a point cloud comprising the gums around the at least one tooth indicated by the second three-dimensional data.

*  *  *  *  *